(12) United States Patent
Mears et al.

(10) Patent No.: US 7,833,275 B2
(45) Date of Patent: *Nov. 16, 2010

(54) METHOD AND APPARATUS FOR PERFORMING A MINIMALLY INVASIVE TOTAL HIP ARTHROPLASTY

(75) Inventors: Dana Mears, Pittsburgh, PA (US); Kevin Greig, Leesburg, IN (US); Paul A Zwirkoski, Brighton, MI (US)

(73) Assignee: Zimmer Technology, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/235,286

(22) Filed: Sep. 26, 2005

(65) Prior Publication Data

US 2006/0030947 A1 Feb. 9, 2006

Related U.S. Application Data

(63) Continuation of application No. 10/053,931, filed on Jan. 22, 2002, now Pat. No. 6,953,480, which is a continuation-in-part of application No. 09/558,044, filed on Apr. 26, 2000, now Pat. No. 6,676,706.

(51) Int. Cl.
*A61F 2/32* (2006.01)
(52) U.S. Cl. ................ 623/22.11; 623/22.15
(58) Field of Classification Search .............. 623/22.11, 623/23.15–23.38, 22.15, 22.21, 22.23; 606/80–81, 606/190
See application file for complete search history.

(56) References Cited

U.S. PATENT DOCUMENTS 3,585,994 A 6/1971 Huggler et al.

(Continued)

FOREIGN PATENT DOCUMENTS

EP 0380309 8/1990

(Continued)

OTHER PUBLICATIONS

Klein, Alan H. and Harry E. Rubash, M.D. "Femoral Windows in Revision Total Hip Arthroplasty." 1993. Clinical Orthopaedics and Related Research, No. 291, pp. 164-170.*

(Continued)

*Primary Examiner*—Thomas C Barrett
*Assistant Examiner*—Nicholas Woodall
(74) *Attorney, Agent, or Firm*—Baker & Daniels LLP

(57) ABSTRACT

A method and apparatus for performing a minimally invasive total hip arthroplasty. An approximately 3.75-5 centimeter (1.5-2 inch) anterior incision is made in line with the femoral neck. The femoral neck is severed from the femoral shaft and removed through the anterior incision. The acetabulum is prepared for receiving an acetabular cup through the anterior incision, and the acetabular cup is placed into the acetabulum through the anterior incision. A posterior incision of approximately 2-3 centimeters (0.8-1.2 inches) is generally aligned with the axis of the femoral shaft and provides access to the femoral shaft. Preparation of the femoral shaft including the reaming and rasping thereof is performed through the posterior incision, and the femoral stem is inserted through the posterior incision for implantation in the femur. A variety of novel instruments including an osteotomy guide; an awl for locating a posterior incision aligned with the axis of the femoral shaft; a tubular posterior retractor; a selectively lockable rasp handle with an engagement guide; and a selectively lockable provisional neck are utilized to perform the total hip arthroplasty of the current invention.

6 Claims, 30 Drawing Sheets

U.S. PATENT DOCUMENTS

| | | | |
|---|---|---|---|
| 3,829,904 A | | 8/1974 | Ling et al. |
| 3,859,669 A | * | 1/1975 | Shersher .................. 623/22.44 |
| 3,955,568 A | | 5/1976 | Neufeld |
| 4,135,517 A | | 1/1979 | Reale |
| 4,341,220 A | | 7/1982 | Perry |
| 4,552,136 A | | 11/1985 | Kenna |
| 4,711,233 A | * | 12/1987 | Brown ......................... 606/81 |
| 4,716,894 A | * | 1/1988 | Lazzeri et al. ................ 606/91 |
| 4,765,328 A | | 8/1988 | Keller et al. |
| 4,903,692 A | | 2/1990 | Reese |
| 4,905,148 A | | 2/1990 | Crawford |
| 5,007,936 A | | 4/1991 | Woolson |
| 5,037,424 A | | 8/1991 | Aboczsky |
| 5,047,034 A | | 9/1991 | Sohngen |
| 5,061,270 A | * | 10/1991 | Aboczky ..................... 606/91 |
| 5,086,401 A | | 2/1992 | Glassman et al. |
| 5,089,003 A | | 2/1992 | Fallin et al. |
| 5,089,004 A | | 2/1992 | Averill et al. |
| 5,127,920 A | * | 7/1992 | MacArthur ............. 623/22.11 |
| 5,139,520 A | * | 8/1992 | Rosenberg .................. 606/87 |
| 5,147,366 A | | 9/1992 | Arroyo et al. |
| 5,152,792 A | | 10/1992 | Watkins et al. |
| 5,156,626 A | | 10/1992 | Broderick et al. |
| 5,177,813 A | | 1/1993 | Bosack et al. |
| 5,190,550 A | | 3/1993 | Miller et al. |
| 5,222,953 A | * | 6/1993 | Dowlatshahi ................ 606/15 |
| 5,242,455 A | | 9/1993 | Skeens et al. |
| 5,251,127 A | | 10/1993 | Raab |
| 5,263,987 A | * | 11/1993 | Shah ........................ 623/18.11 |
| 5,284,483 A | | 2/1994 | Johnson |
| 5,295,694 A | * | 3/1994 | Levin ......................... 273/447 |
| 5,299,288 A | | 3/1994 | Glassman et al. |
| 5,305,203 A | | 4/1994 | Raab |
| 5,320,625 A | * | 6/1994 | Bertin ......................... 606/91 |
| 5,324,366 A | | 6/1994 | Keil et al. |
| 5,339,803 A | | 8/1994 | Mayzels et al. |
| 5,342,363 A | | 8/1994 | Richelsoph |
| 5,360,446 A | | 11/1994 | Kennedy |
| 5,364,403 A | | 11/1994 | Petersen et al. |
| 5,383,454 A | | 1/1995 | Bucholz |
| 5,389,101 A | | 2/1995 | Heilbrun et al. |
| 5,408,409 A | | 4/1995 | Glassman et al. |
| 5,441,059 A | * | 8/1995 | Dannan ....................... 128/898 |
| 5,474,560 A | | 12/1995 | Rohr, Jr. |
| 5,490,852 A | | 2/1996 | Azer et al. |
| 5,507,814 A | | 4/1996 | Gilbert et al. |
| 5,507,830 A | | 4/1996 | DeMane et al. |
| 5,517,990 A | | 5/1996 | Kalfas et al. |
| 5,540,692 A | | 7/1996 | Tidwell |
| 5,571,111 A | | 11/1996 | Aboczky |
| 5,578,037 A | | 11/1996 | Sanders et al. |
| 5,607,431 A | | 3/1997 | Dudasik et al. |
| 5,616,147 A | | 4/1997 | Gadelius |
| 5,624,447 A | | 4/1997 | Myers |
| 5,658,294 A | | 8/1997 | Sederholm |
| 5,676,673 A | | 10/1997 | Ferre et al. |
| 5,682,886 A | | 11/1997 | Delp et al. |
| 5,683,395 A | | 11/1997 | Mikhail |
| 5,690,635 A | | 11/1997 | Matsen, III et al. |
| 5,720,750 A | | 2/1998 | Koller et al. |
| 5,738,586 A | | 4/1998 | Arriaga |
| 5,741,215 A | | 4/1998 | D'Urso |
| 5,741,261 A | * | 4/1998 | Moskovitz et al. ............ 606/79 |
| 5,748,767 A | | 5/1998 | Raab |
| 5,769,092 A | | 6/1998 | Williamson, Jr. |
| 5,776,064 A | | 7/1998 | Kalfas et al. |
| 5,788,704 A | | 8/1998 | Timperley |
| 5,800,352 A | | 9/1998 | Ferre et al. |
| 5,803,089 A | | 9/1998 | Ferre et al. |
| 5,806,518 A | | 9/1998 | Mittelstadt |
| 5,814,050 A | * | 9/1998 | Benson ...................... 606/102 |
| 5,817,105 A | | 10/1998 | VanDerBrug |
| 5,824,083 A | | 10/1998 | Draenert |
| 5,824,085 A | | 10/1998 | Sahay et al. |
| 5,829,444 A | | 11/1998 | Ferre et al. |
| 5,871,018 A | | 2/1999 | Delp et al. |
| 5,871,445 A | | 2/1999 | Bucholz |
| 5,879,353 A | | 3/1999 | Terry |
| 5,879,406 A | | 3/1999 | Lilley |
| 5,885,295 A | | 3/1999 | McDaniel et al. |
| 5,935,141 A | | 8/1999 | Weldon |
| 5,950,629 A | | 9/1999 | Taylor et al. |
| 5,951,561 A | | 9/1999 | Pepper et al. |
| 5,954,727 A | | 9/1999 | Collazo |
| 5,997,582 A | | 12/1999 | Weiss |
| 6,010,535 A | | 1/2000 | Shah |
| 6,022,354 A | * | 2/2000 | Mercuri et al. ................ 606/80 |
| 6,027,505 A | | 2/2000 | Peter et al. |
| 6,050,266 A | | 4/2000 | Benetti et al. |
| 6,063,088 A | | 5/2000 | Winslow |
| 6,113,605 A | | 9/2000 | Storer |
| 6,120,508 A | | 9/2000 | Grunig et al. |
| 6,231,611 B1 | * | 5/2001 | Mosseri ................... 623/22.12 |
| 6,264,698 B1 | | 7/2001 | Lawes et al. |
| 6,395,005 B1 | | 5/2002 | Lovell |
| 6,991,656 B2 | | 1/2006 | Mears |
| 2001/0014828 A1 | | 8/2001 | Yoon |
| 2001/0014829 A1 | | 8/2001 | Yoon |
| 2001/0016780 A1 | | 8/2001 | Yong San |
| 2002/0128659 A1 | | 9/2002 | Michelson |
| 2003/0050645 A1 | | 3/2003 | Parker et al. |
| 2003/0158559 A1 | | 8/2003 | Diaz |
| 2003/0195517 A1 | | 10/2003 | Michelson |
| 2003/0220698 A1 | | 11/2003 | Mears et al. |
| 2003/0229356 A1 | | 12/2003 | Dye |
| 2004/0034358 A1 | | 2/2004 | Michelson |

FOREIGN PATENT DOCUMENTS

| | | |
|---|---|---|
| EP | 0558203 | 9/1993 |
| EP | 0956824 | 11/1999 |
| EP | 1149562 | 10/2001 |
| EP | 1258233 | 11/2002 |
| EP | 0956824 | 3/2004 |
| EP | 1149562 | 8/2006 |
| FR | 1041311 | 8/1951 |
| FR | 1041311 | 10/1953 |
| FR | 2721192 | 12/1995 |
| FR | 2742038 | 6/1997 |
| FR | 2775889 | 6/1999 |
| FR | 2775889 | 9/1999 |
| JP | 59-200643A A | 11/1984 |
| JP | 04-044758A A | 2/1992 |
| JP | 10-328205A A | 12/1998 |
| WO | 03065906 | 8/2003 |
| WO | WO03/065906 | 8/2003 |

OTHER PUBLICATIONS

The Elevated-Rim Acetabular Liner in Total Hip Arthroplasty: Relationship to Postoperative Dislocation by T.K. Cobb, M.D. et al.

Displacement after Total Hip-Replacement Arthroplasties by George E. Lewinnek, M.D. et al.

Range of Motion in Contemporary Total Hip Arthroplasty by Robert J. Krushell, M.D. et al.

Elevated-Rim Acetabular Components by Robert J. Krushell, M.D. et al.

Range of Motion Studies for Total Hip Replacements by Harlan C. Amstutz. M.D. et al.

Dislocation After Total Hip Arthroplasty by Donald E. McCollum, M.D. et al.

Finite Element Modeling of Dislocation Propensity in Total Hip Arthroplasty by T.A. Maxian et al.

Femoral Head Containment in Total Hip Arthroplasty, Standard v. Extended Lip Liners by T.D. Brown et al.

An Image-Directed Robotic System for Precise Orthopaedic Surgery by Russell H. Taylor et al.

Techniques for Fast and Accurate Intrasurgical Registration by David A. Simon et al.

Computer-Assisted Knee Anterior Cruciate Ligament Reconstruction: First Clinical Tests by Vincent Dessenne et al.

Comparison of Relative Accuracy Between a Mechanical and an Optical Postion Tracker for Image-Guided Neurosurgery by Robert Rohling et al.

Computer-Assisted Spine Surgery: A Technique for Accurate Transpedicular Screw Fixation Using CT Data and a 3-D Optical Localizer by S. Lavallee et al.

Etude Du Cotyle Non Scelle De Bousquet Dans Cent Protheses Totales De Hanche Hybrides by J.H. Aubriot et al.

La Tige Vissee De Bousquet Dans L'Arthroplastie Totale De Hanche En Premiere Intention by M.H. Fessy et al.

Anatomy-based Registration for Computer-Integrated Surgery by Ali Hamadeh et al.

BIAS Total Hip System Surgical Technique for Premary Hip Arthroplasty and Revision of Hip Arthroplasty with Bone Grafting by Ramon B. Gustilo. M.D. et al.

Kenneth A. Krackow, M.D. et al.: "Clinical Experience with a Triradiate Exposure of the Hip for Difficult Total Hip Arthroplasty", pp. 267-278, The Journal of Arthroplasty, Sep. 1988.

Pasquale Petrera, M.D. et al.: "Revision Total Hip Arthroplasty with a Retroperitoneal Approach to the Iliac Vessels", The Journal of Arthroplasty, 1996, pp. 704-708.

G. Lang et al.: "Arthroplasty of the hip by cemented coupled cups", 1978, Masson, Paris, Nouv. Presse Med., pp. 3925-3928.

J.C. Boa et al.: "The surgical anatomy of the superior gluteal nerve and anatomical radiologic bases of the direct lateral approach to the hip" Surgical Radiologic Anatomy, 1994, pp. 253-258.

Mansho Itokazu et al.: "Exposure of the Hip by Anterior Osteotomy of the Greater Trochanter", Hospital for Joint Diseases Bulletin, 1998, pp. 159-161.

John J. Joyce, III et al.: "The Anatomical Basis of the Hip Joint Exposures", No. 98, Jan.-Feb. 1974, pp. 27-31.

"Surgery of the Hip Joint", Edited by Raymond G. Tronzo, M.D., Copyright 1873, Lea & Febiger, Philadelphia.

Journal of the Japanese Orthopedic Association 75 (2), 2001: Kazuo Kaneko et al., "Total Hip Arthroplasty and Femoral Head Prosthetic Replacement Using Mini Incisions" and Shoichi Shinoda et al., "Joint Use of Acetabular Abduction Osteotomy and Anterior Trochantic Slide for Osteoarthritis of the Hip Joint".

Ralph Lusskin et al. "Combined Anterior and Posterior Approach to the Hip Joint in Reconstructive and Complex Arthroplasty". Department of Orthopedic Surgery, New York University Medical Center, New York, NY Dec. 1988, pp. 313-322.

James B. Stiehl et al.: "Extensile Triradiate Approach for Complex Acetabular Reconstruction in Total Hip Arthroplasty", Clinical Orthopaedics and Related Research, 1993, pp. 162-169.

Richard H. Walker, M.D.: "Pelvic Reconstruction/Total Hip Arthroplasty for Metastatic Acetabular Insufficiency", Clinical Orthopaedics and Related Research, 1993, pp. 170-175.

Joel M. Matta, M.D.: "Operative Treatment of Acetabular Fractures Through the Ilioinguinal Approach, a 10=year Perspective", Clinical Orthopaedics and Related Research, 1994, pp. 10-19.

http://www.orthoteers.co.uk, "Pelvis & Acetabulun-Surgical Approaches", 3 pages, Jan. 2001.

Robert E. Kennon el al.: "Total Hip Arthroplasty Using the Minimally Invasive Anterior Surgical Approach", Yale University School of Medicine, Department of Orthopaedics & Rehabilitation.

http://www.orthoteers.co.uk, "Hip-Surgical Approaches", 9 pages, Jan. 2001.

Video Tape—Cementless Ceramic Hip Replacement: The Anterior Approach, Kristaps Keggi, M.D., Jun. 1, 1985.

Curriculum Vitae of Dr. Kristaps Juris Keggi.

Article—Anterior Approach to Hip Arthroplasty, Terry R. Light, M.D., et al., Clinical Orthopaedics and Related Research, pp. 225-260.

Reference—"The Yale Journal of Biology and Medicine", vol. 66, No. 3, May-Jun. 1993, pp. 243-256.

Article—"Superior Mesenteric Vein Tear with Total Hip Arthroplasty", Jonathan N. Grauer, M.D., et al., The Journal of Arthroplasty vol. 16, No. 5, 2001, pp. 671-673.

Article—"Total Hip Arthroplasty Using the Sweymuller Stem Implanted Without Cement", Michael H. Huo, M.D., et al., The Journal of Arthroplasty vol. 10, No. 6, 1995, pp. 793-799.

Article—"Total Hip Replacement Update: Cement v Cementless Arthroplasty", Ronald W. Lindsey, M.D., et al., Connecticut Medicine, vol. 52, No. 7, Jul. 1988, pp. 399-401.

Article—"Primary Ceramic Hip replacement: A Prospective Study of 119 Hips", Scott A. Hoffinger, M.D., el al., Orthopedics, May 1991, vol. 14, pp. 523-531.

Article—"Anatomy and Osteotomy of the Greater Trochanter", John P. Fulkerson, M.D., et al., Archives of Surgery, vol. 114, Jan. 1979, pp. 19-21.

Article—"One-Stage Bilateral Total Hip Arthroplasty in Patients > 75 Years", Marc A. Weinstein, M.D., et al., Orthopedics, vol. 25, No. 2, Feb. 2002, pp. 153-156.

Article—"A Comparison of the Cost Effectiveness of One-Stage Versus Two-Stage Bilateral Total Hip Replacement", Mark Lorenze, M.D., et al., Orthopedics, vol. 21, No. 12, Dec. 1998, pp. 1249-1252.

Surgical Exposure and Cement Removal in Revision Total Hip Arthroplasty, Thomas H. Mallory, Seminars in Arthroplasty, col. 3, No. 4, Oct. 1992, pp. 257-263.

Mini-Incision for Total Hip Arthroplasty, John M. Wright, M.D., et al., Orthopedic Special Edition, vol. 7, No. 2 of 2, 2001, pp. 18-20.

Robotics for Surgery, Robert D. Howe et al., Annual Rev. Biomed. Eng. 1999, pp. 211-240.

Minimally Invasive Total Hip Arthroplasty, George F. Chimento, M.D., et al., Operative Techniques in Orthopaedics, vol. 11, No. 4, Oct. 2001, pp. 270-273.

Application of Arthroplasty Principles to Canine Cemented Total Hip Replacement, Kurt S. Schultz, Veterinary Surgery, 2000, pp. 578-593.

Anterior Approach to Resurfacing Arthroplasty of the Hip: a Preliminary Experience, Robert P. Hendrikson, M.D., et al., Connecticut Medicine, Mar. 1983, vol. 47, No. 3, pp. 131-135.

A New Era of Minimally Invasive Surgical Approaches for THA, Timothy McTighe, Ph.D., Joint Implant Surgery and Research Foundatino, Dec. 2002, pp. 2-7.

The Office Action mailed May 12, 2009 in related Japanese application No. 2004-028295.

The Office Action mailed Aug. 18, 2009 in related Japanese application No. 2001-129998.

The Office Action mailed Aug. 19, 2008 in related Japanese application No. 2001-129998.

The European Office Action mailed Feb. 28, 2006 in related European application No. 04000194.3.

The Response filed Jun. 22, 2006 to the European Office Action mailed Feb. 28, 2006 in related European application No. 04000194.3.

The European Office Action mailed Aug. 30, 2005 in related European application No. 04000194.3.

The Response filed Jan. 6, 2006 to the European Office Action mailed Aug. 30, 2005 in related European application No. 04000194.3.

The European Search published Apr. 14, 2004 in related European application No. 04000194.3.

The Canadian Office Action mailed Jun. 18, 2009 in related Canadian application No. 2,343,926.

The Response filed Feb. 19, 2009 to the Canadian Office Action mailed Aug. 22, 2008 in related Canadian application No. 2,343,926.

The Canadian Office Action mailed Aug. 22, 2008 in related Canadian application No. 2,343,926.

The European Office Action mailed Aug. 16, 2009 in related European application No. 04250522.2.

The Response filed Aug. 26, 2009 to the European Office Action mailed Feb. 16, 2009 in related European application No. 04250522.2.

* cited by examiner

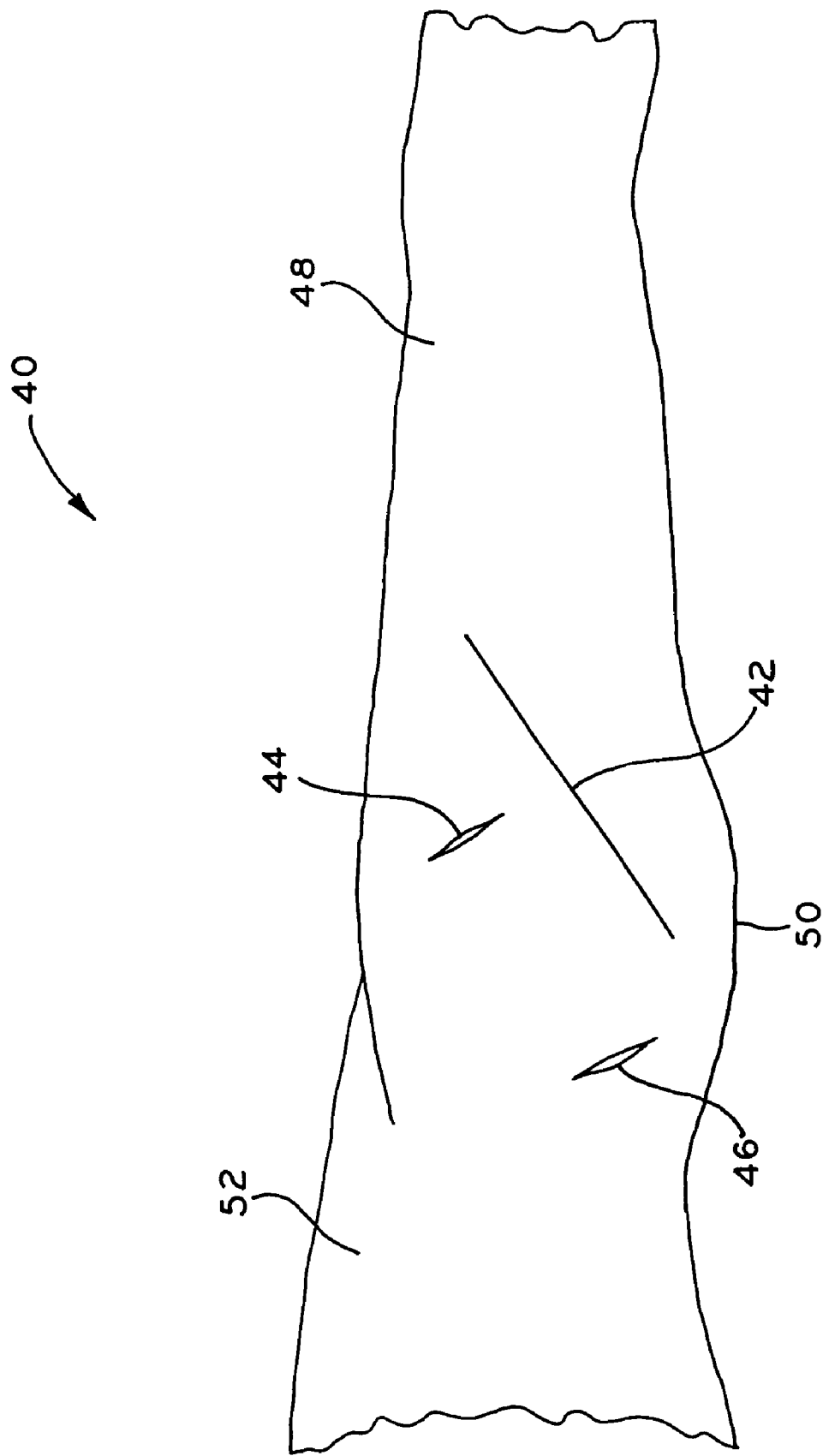

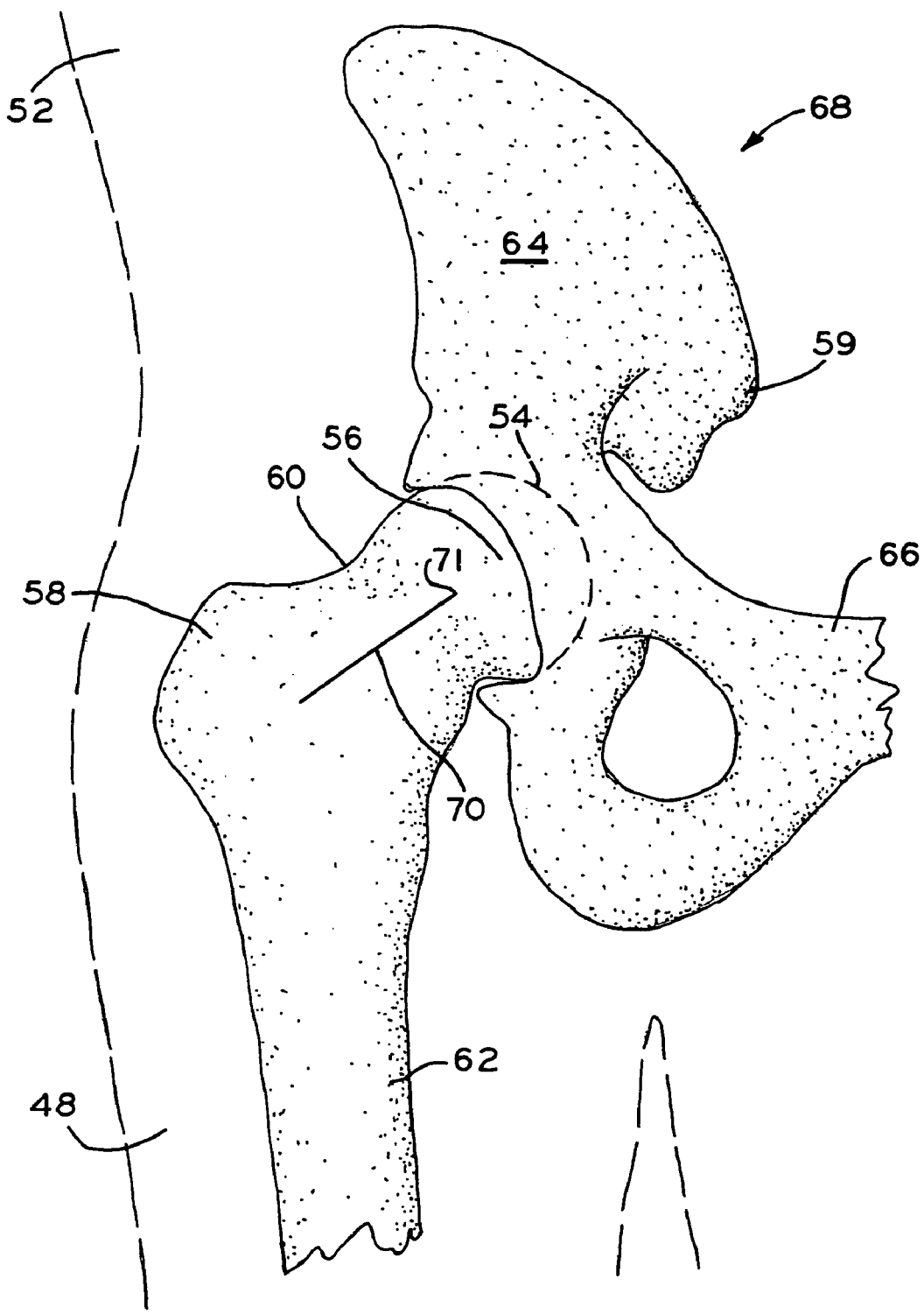
FIG_2

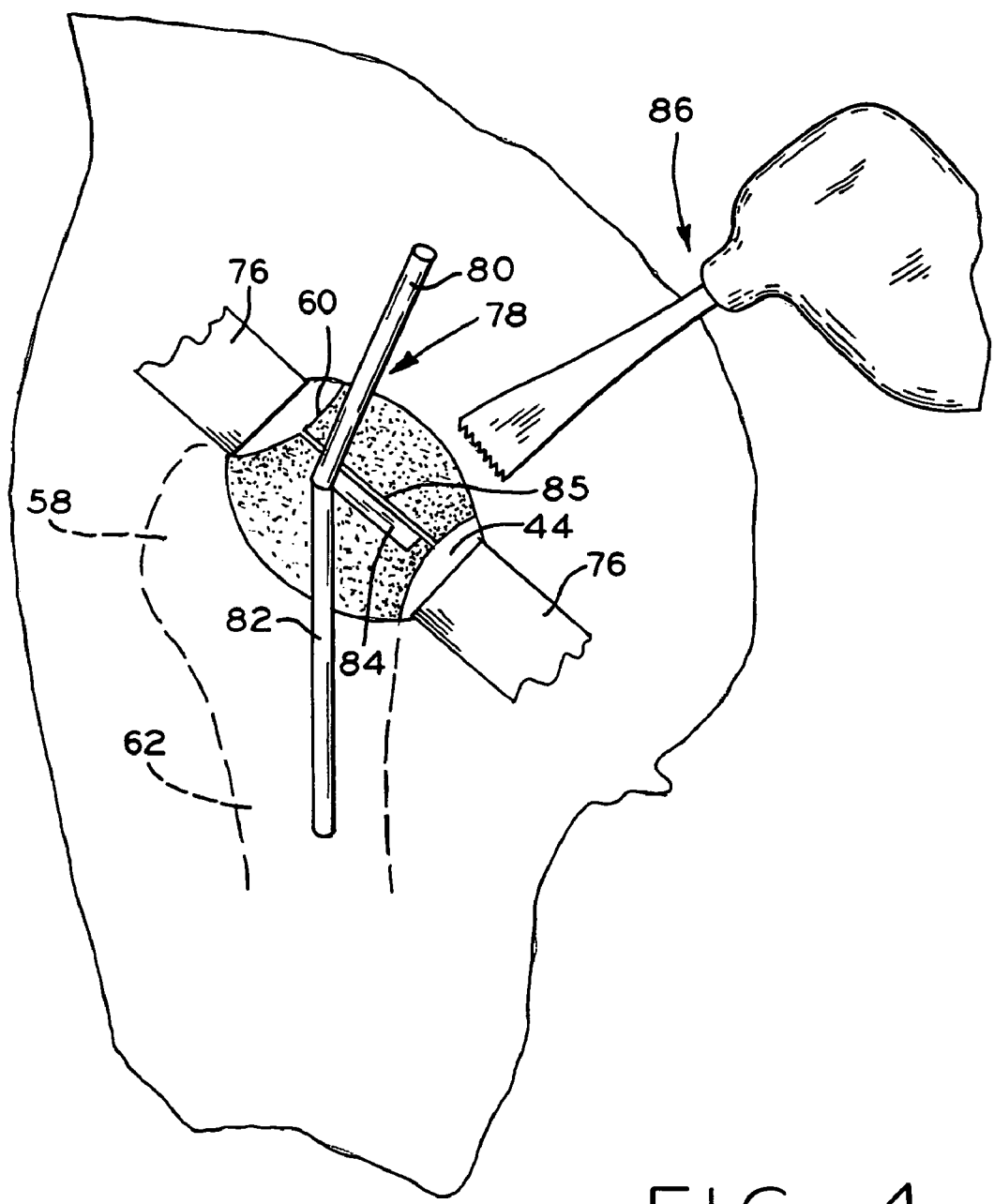
FIG_ 4

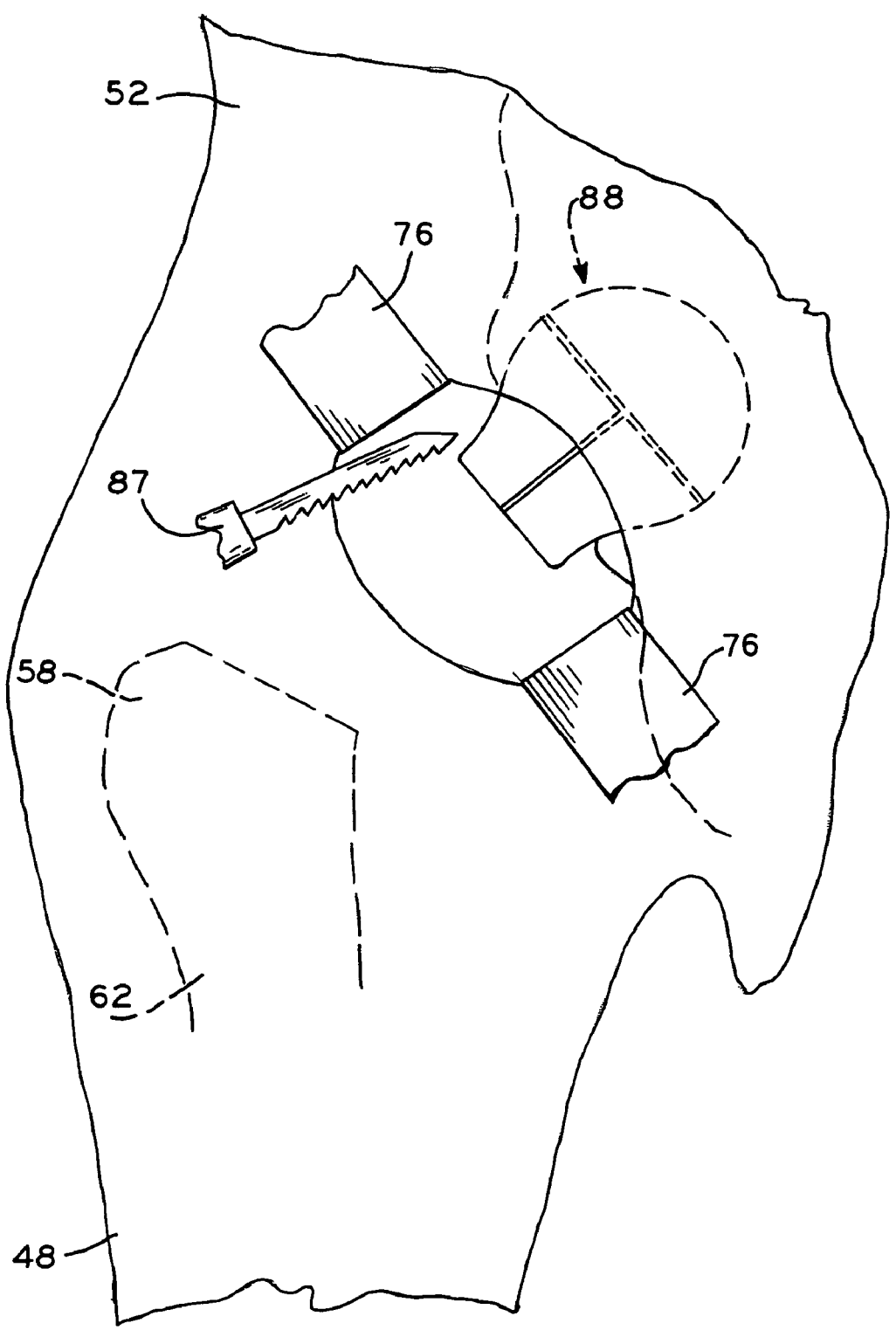
FIG_6

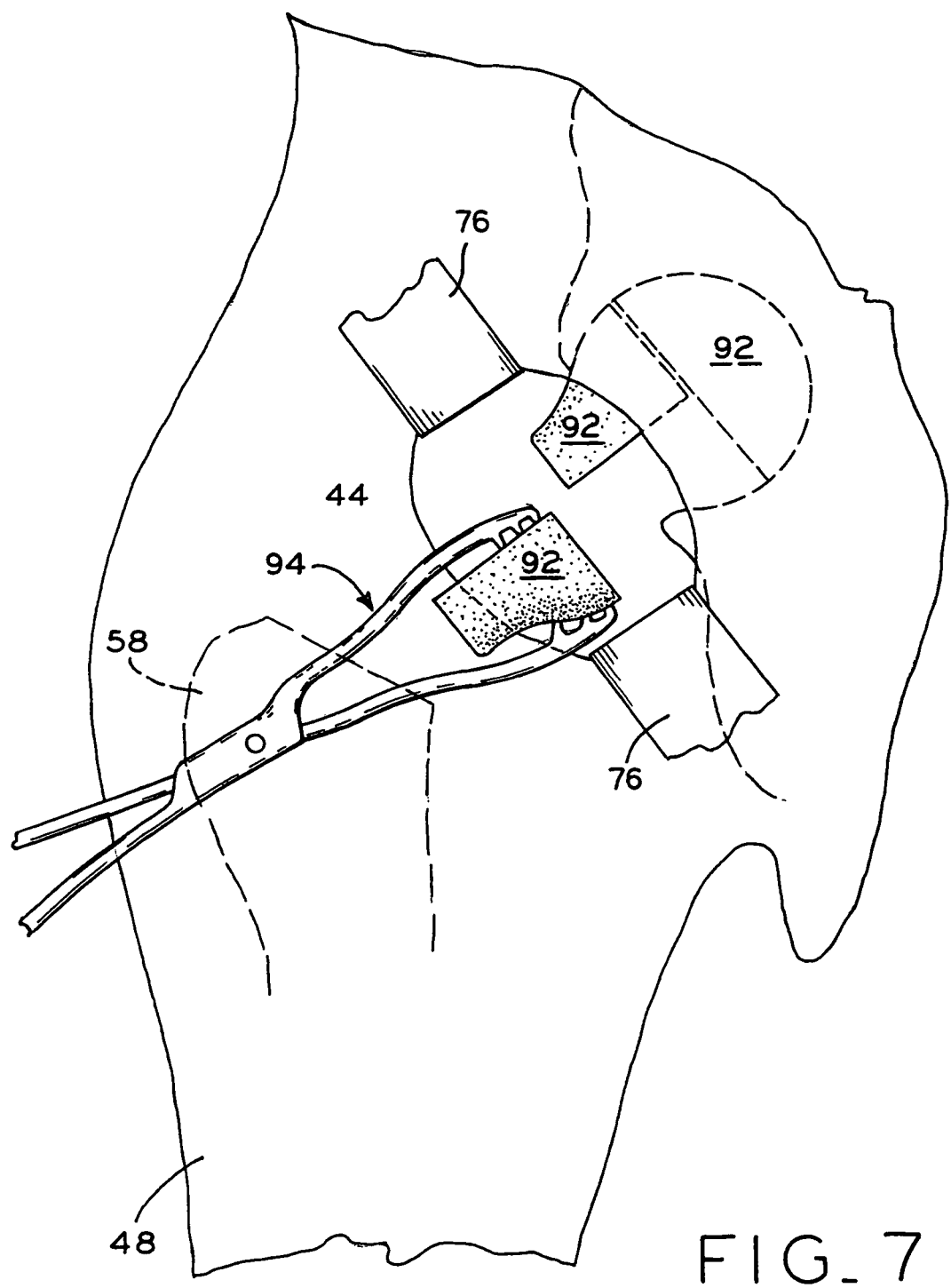
FIG_7

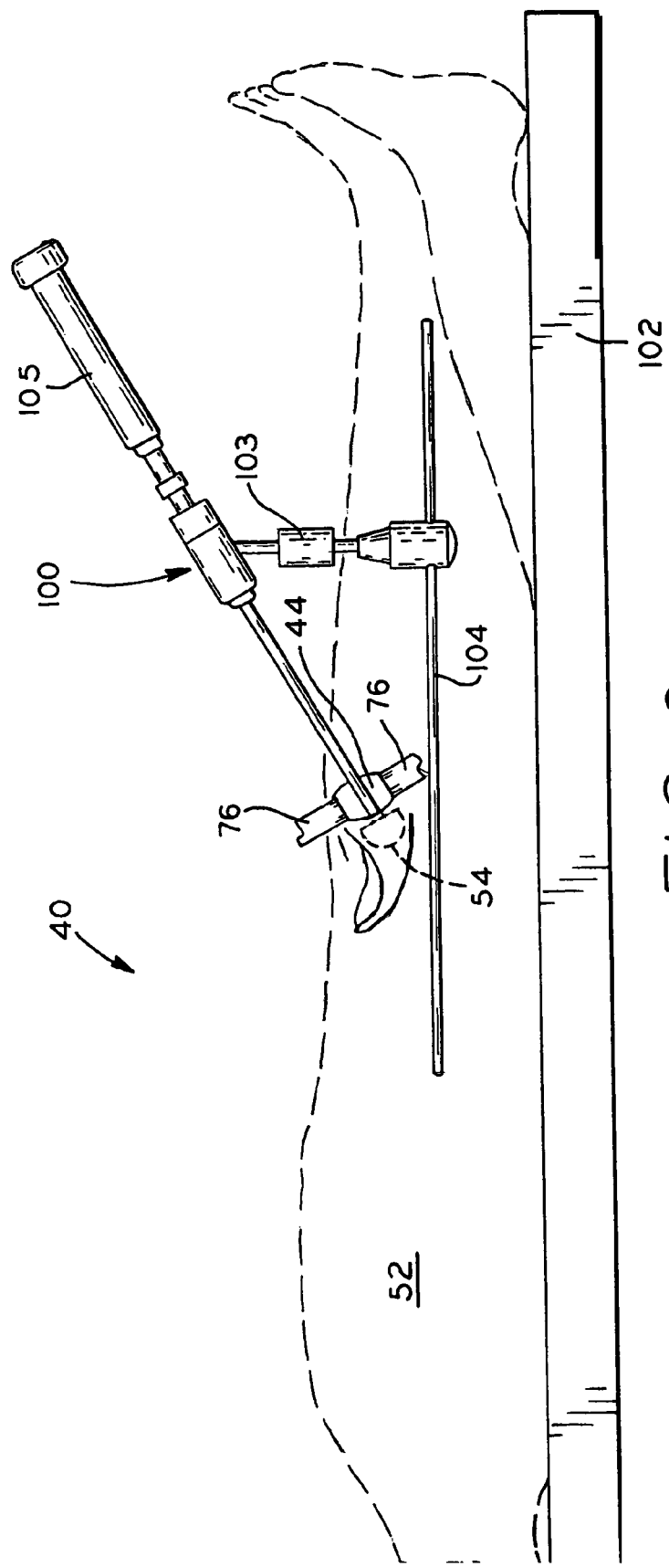

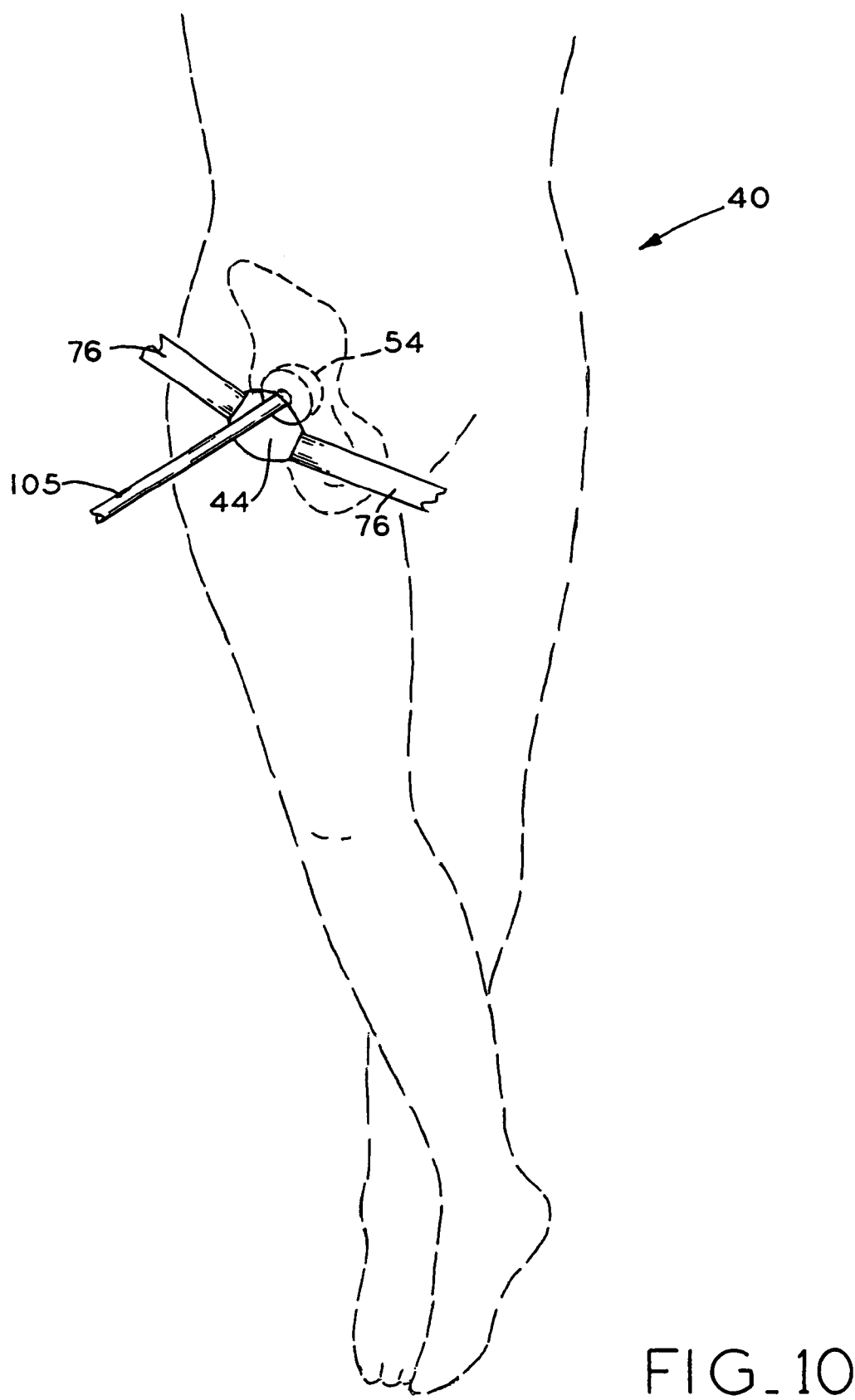
FIG_10

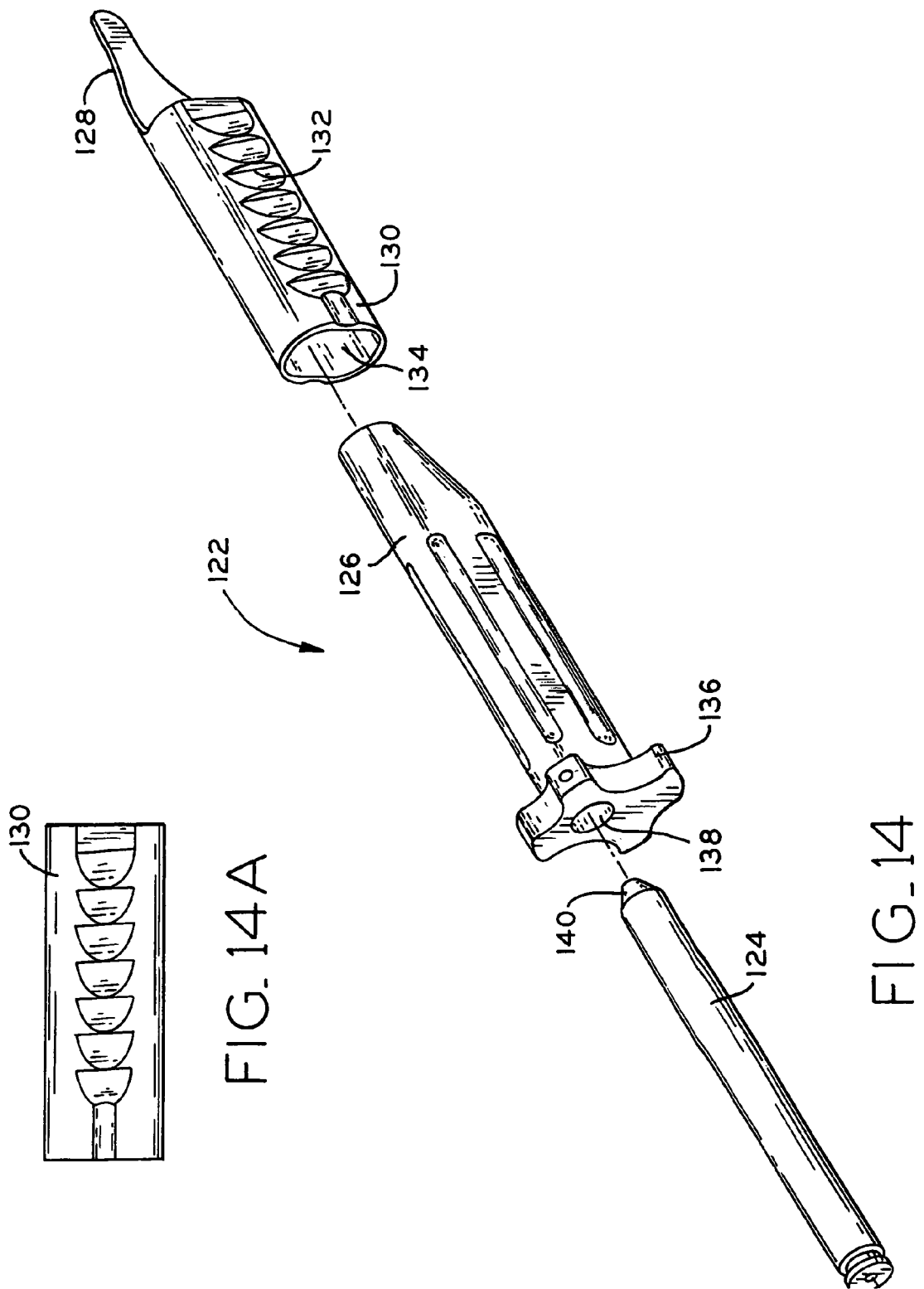

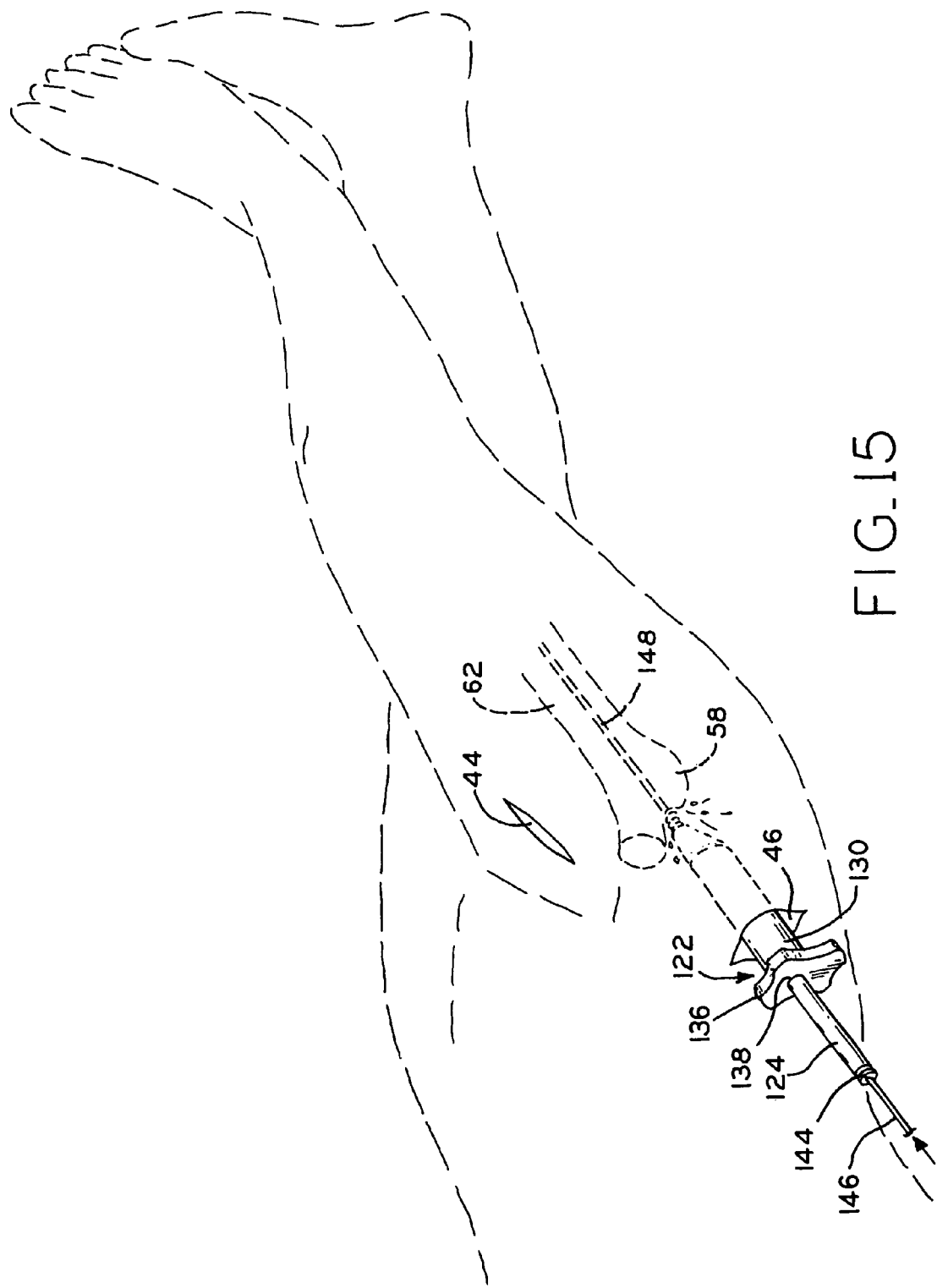

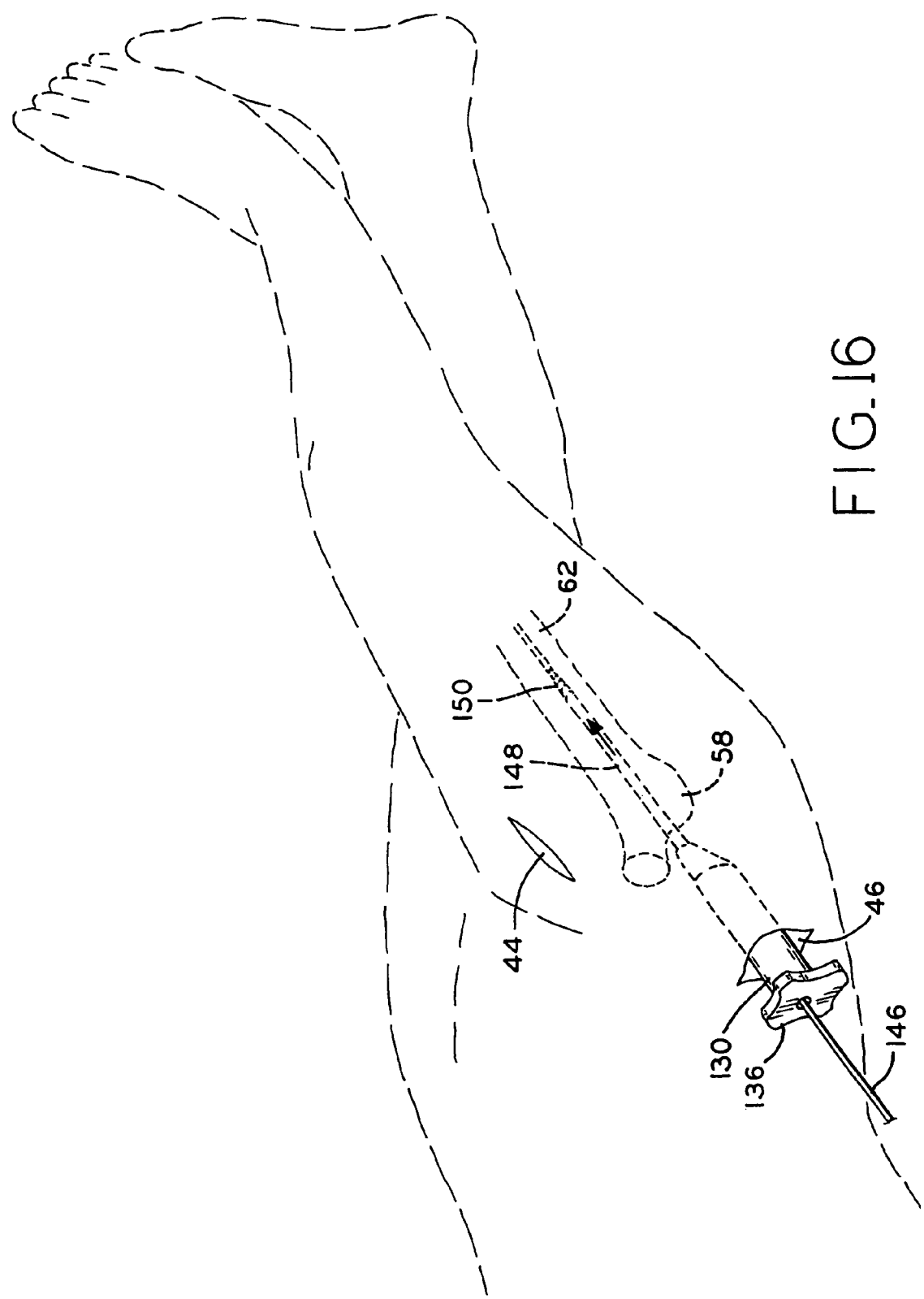

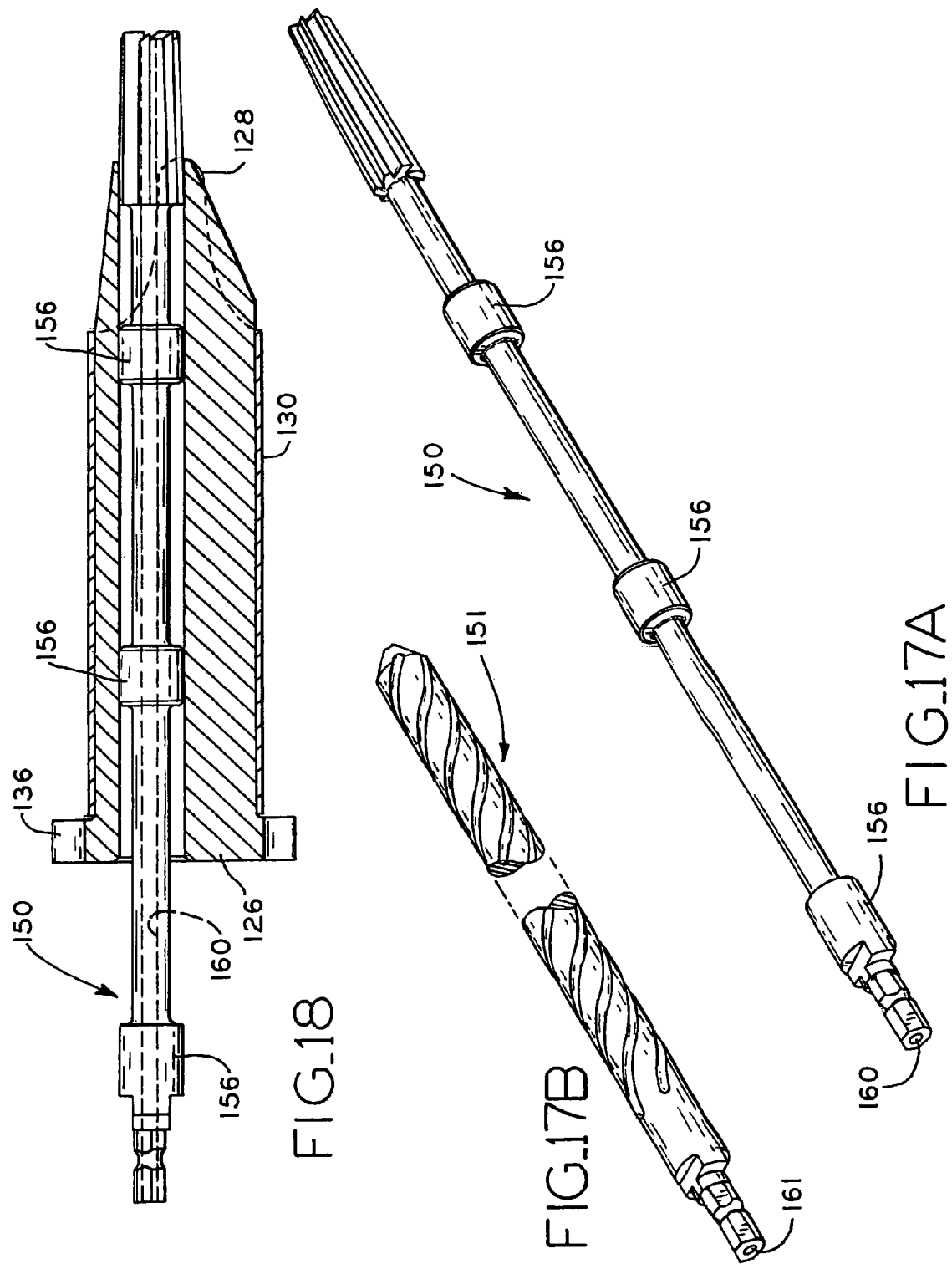

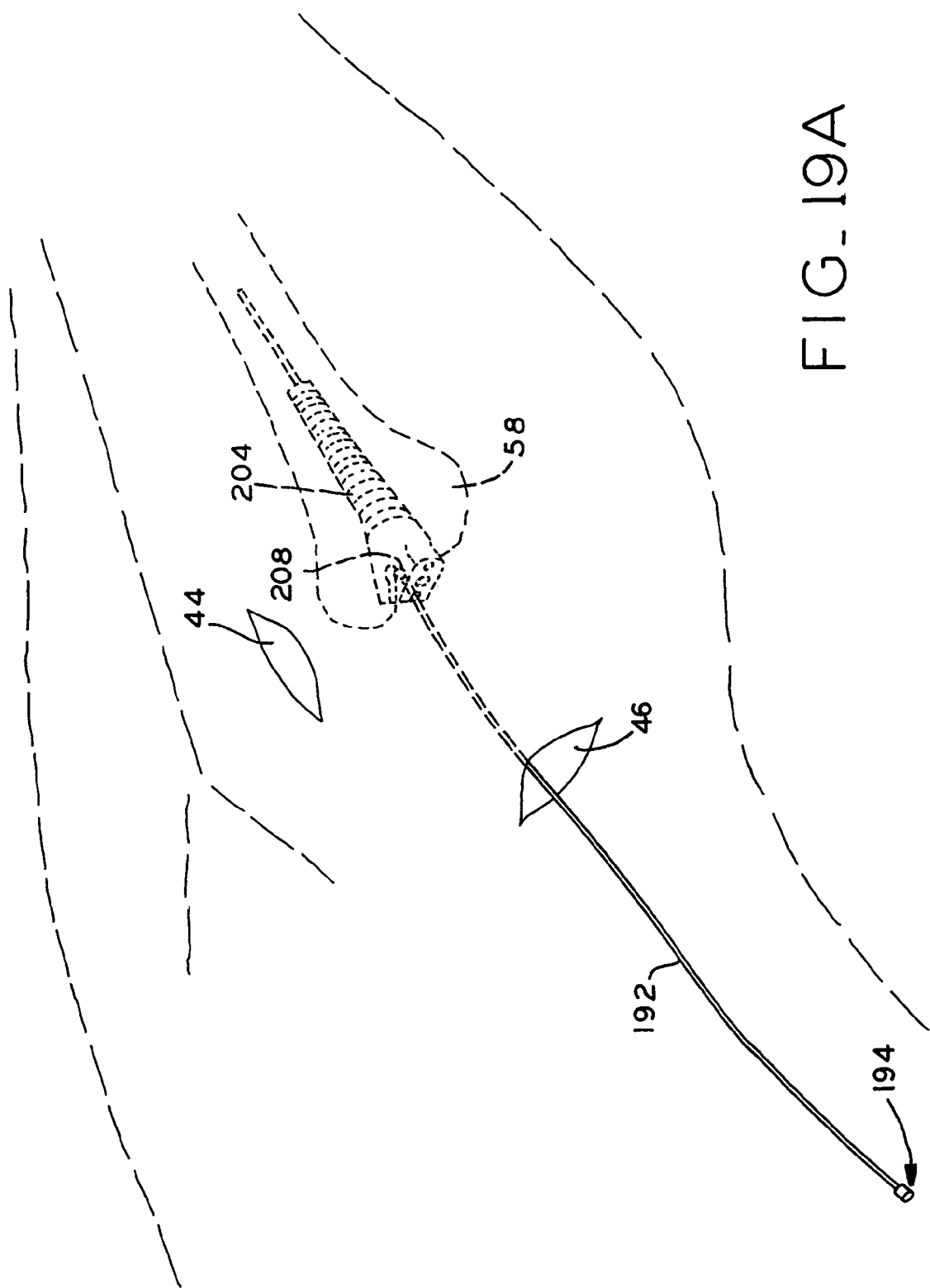

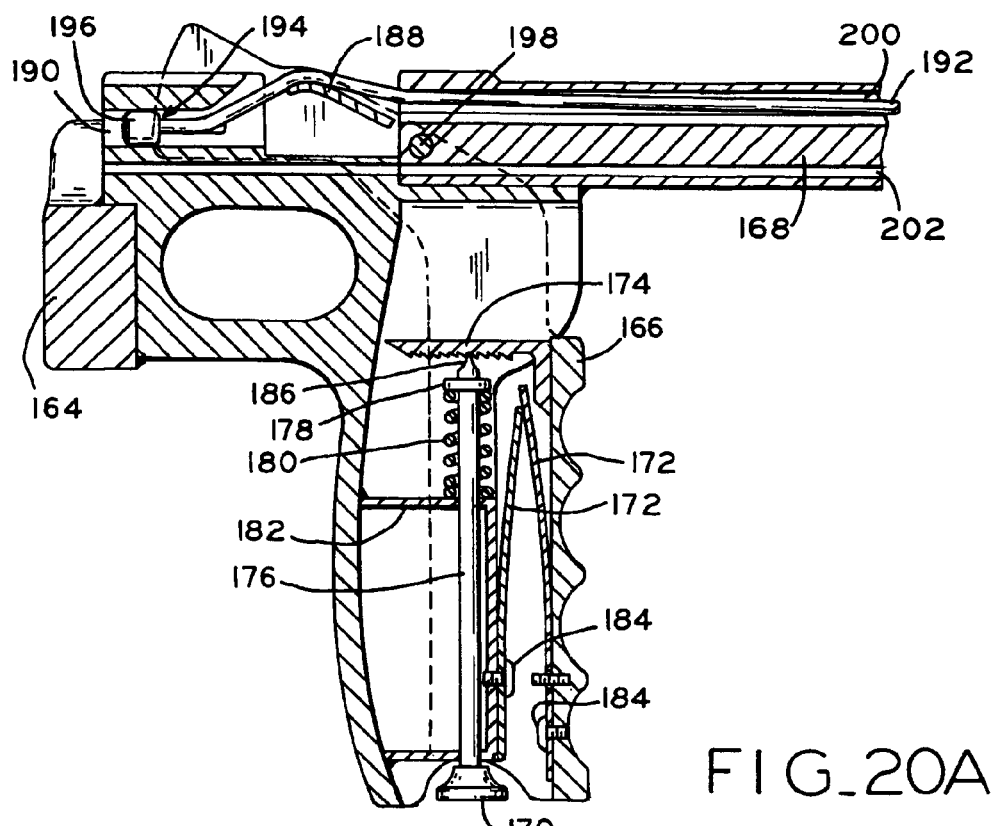
FIG_20A
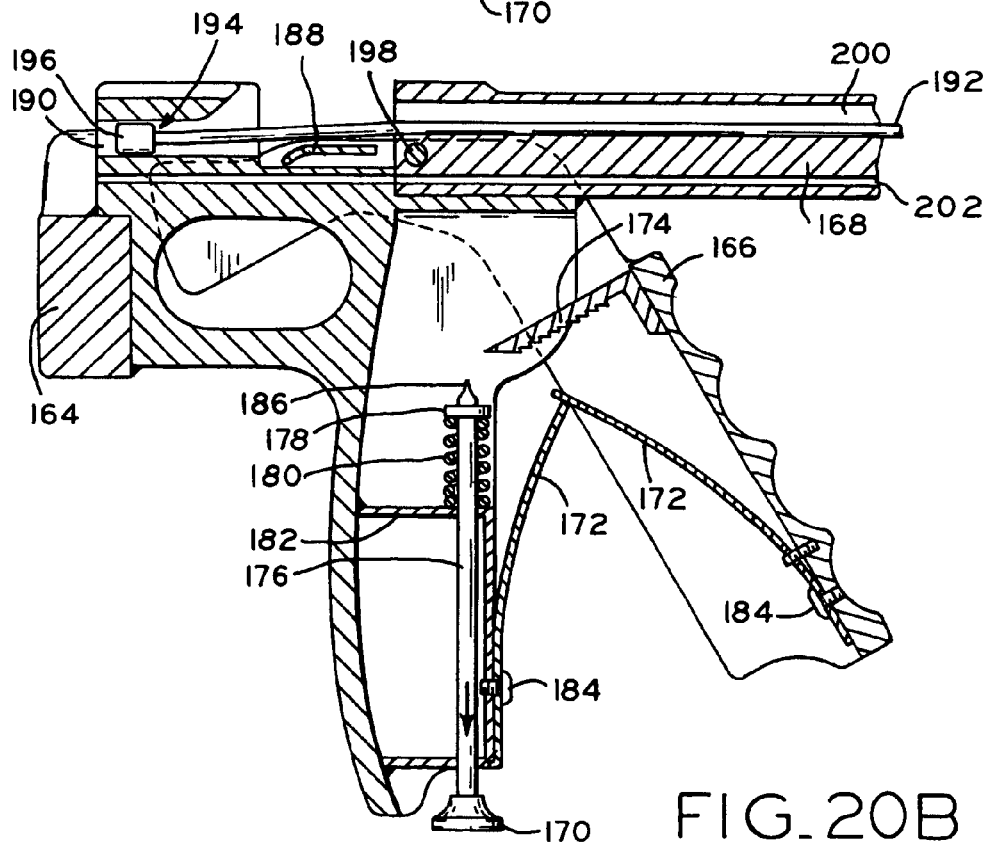
FIG_20B

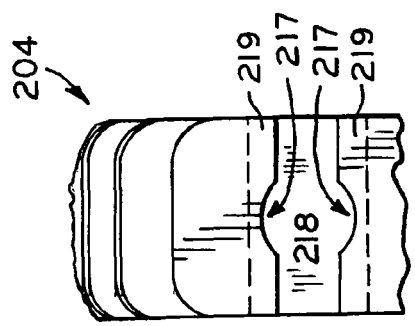
FIG. 21A
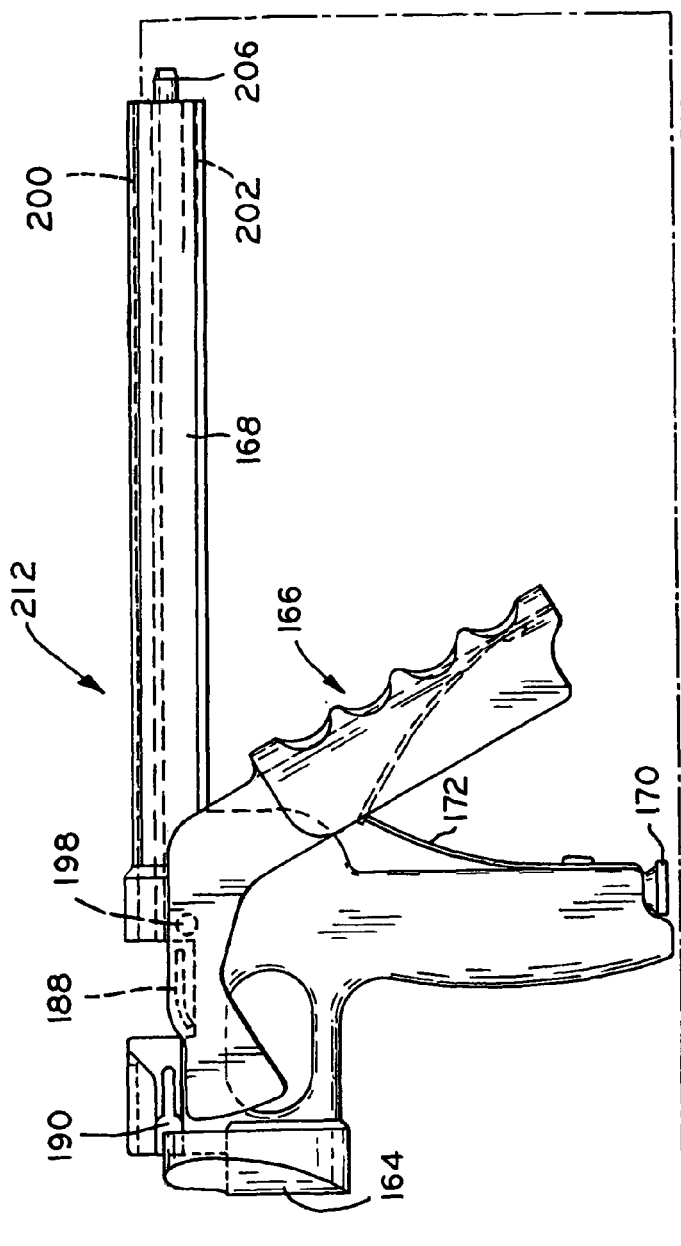
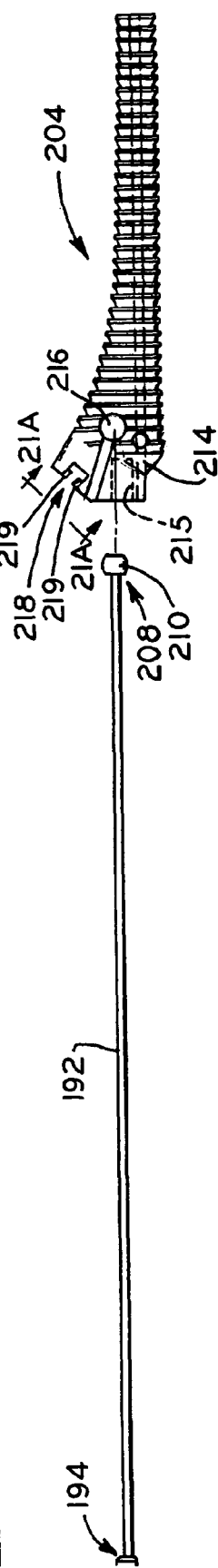
FIG. 21

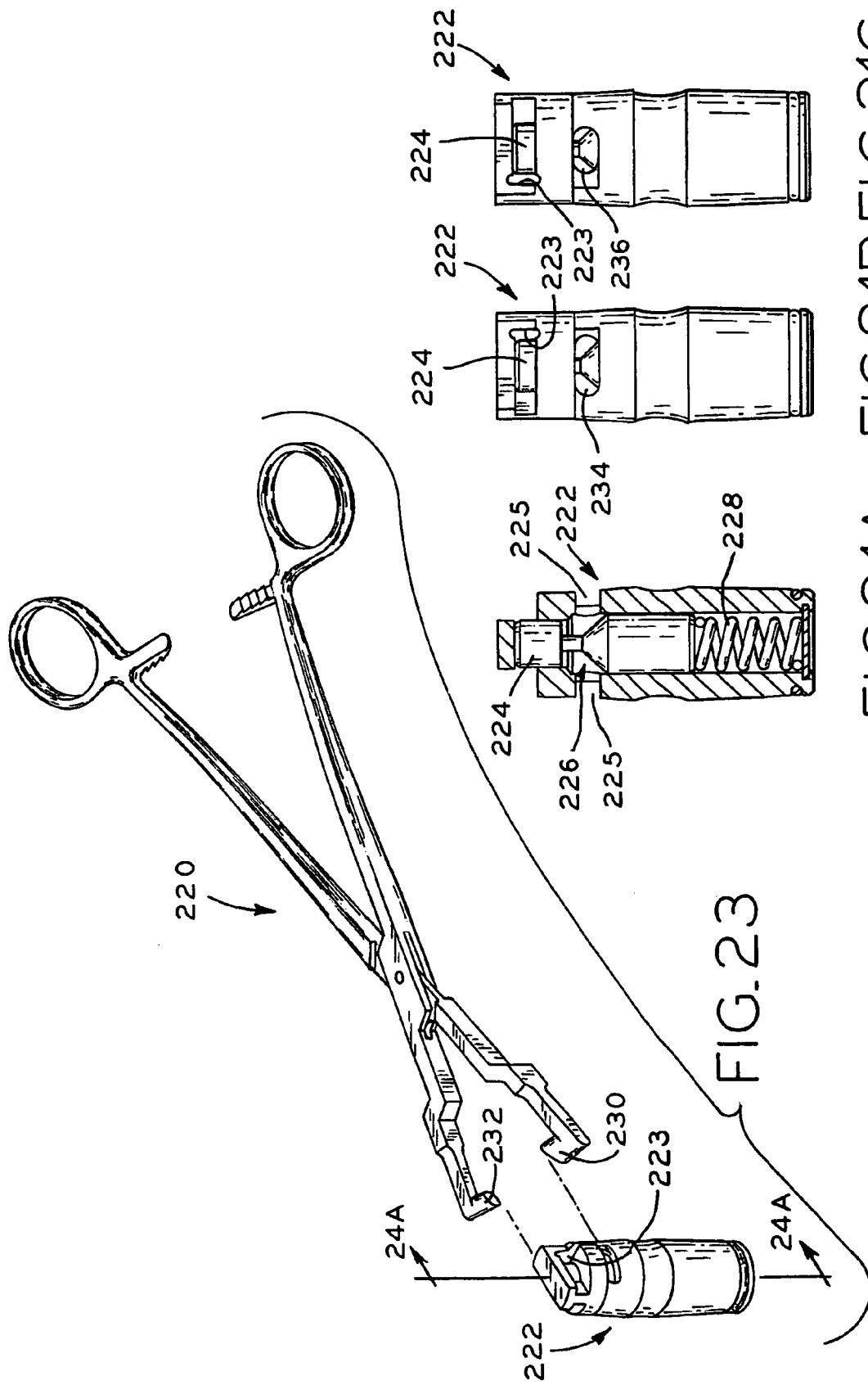

FIG_27

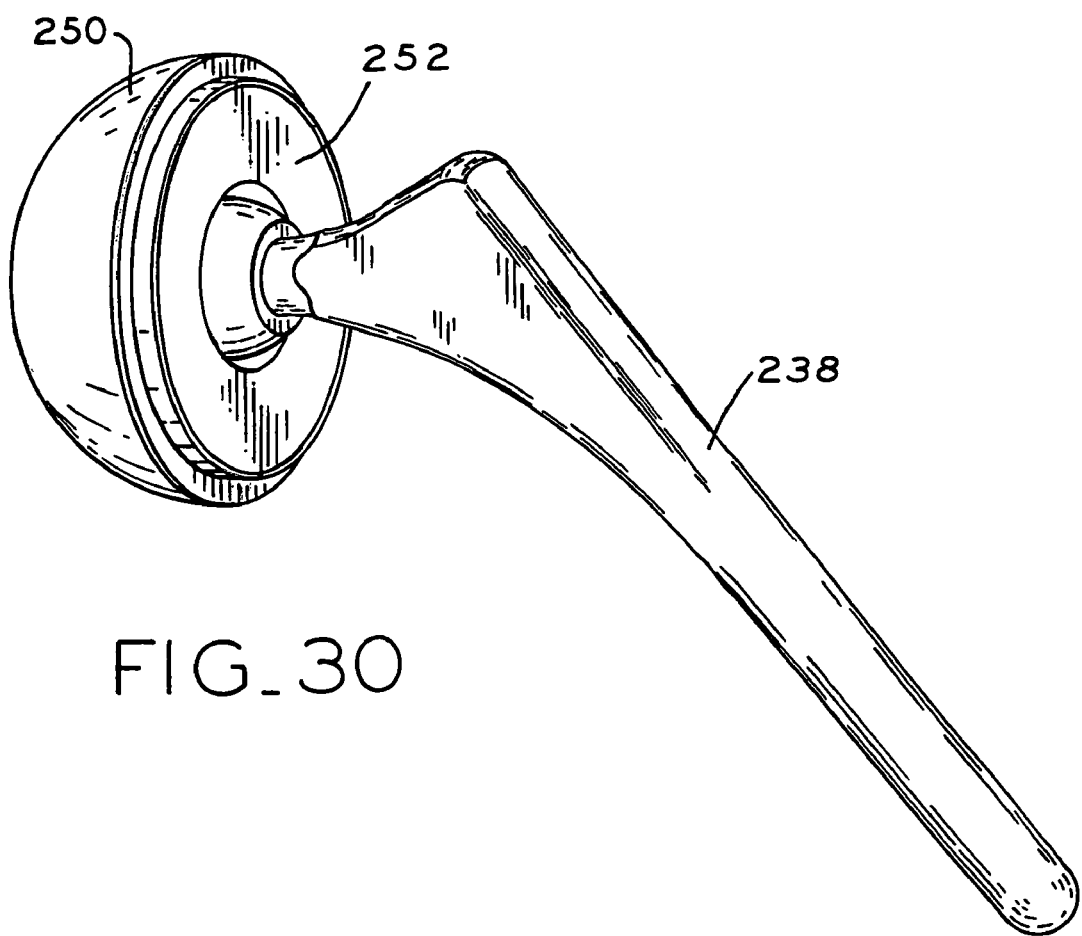
FIG_30

METHOD AND APPARATUS FOR PERFORMING A MINIMALLY INVASIVE TOTAL HIP ARTHROPLASTY

CROSS-REFERENCE TO RELATED APPLICATIONS

This application is a Continuation of U.S. patent application Ser. No. 10/053,931 filed Jan. 22, 2002 (now U.S. Pat. No. 6,953,480), which is a continuation-in-part of application Ser. No. 09/558,044 filed on Apr. 26, 2000 (now U.S. Pat. No. 6,676,706), the disclosures of which are hereby explicitly incorporated by reference herein.

BACKGROUND OF THE INVENTION

1. Field of the Invention

The present invention relates to total hip arthroplasty, and, more particularly, to a method and apparatus for performing a minimally invasive total hip arthroplasty.

2. Description of the Related Art

Orthopaedic procedures for the replacement of all, or a portion of, a patient's joint have been developed over the last 30 years. Currently, the procedures used to prepare the bone and seat the implants are generally referred to as open procedures. For the purpose of this discussion, the term open procedure will refer to a procedure wherein an incision is made through the skin and underlying tissue to fully expose a large portion of the particular joint surface. In the case of a total hip arthroplasty, the typical incision required is approximately 25 centimeters (10 inches) long. After the initial incision in the skin, the internal wound may be enlarged in order to fully expose the areas to be prepared. While this approach provides surgeons with an excellent view of the bone surface, the underlying damage to the soft tissue, including the muscles, can lengthen a patient's rehabilitation time after surgery. While the implants may be well fixed at the time of surgery, it may be several weeks or perhaps months before the soft tissues violated during surgery can be fully healed.

SUMMARY OF THE INVENTION

The present invention provides an improved method and apparatus for performing a minimally invasive total hip arthroplasty. A total hip arthroplasty can be performed in accordance with the teachings of the current invention utilizing two incisions with the size of each of the wounds developed on the surface being substantially constant throughout the depth of the wound. The first incision is an anterior incision approximately 3.75-5 centimeters (1.5-2 inches) in length made in line with the femoral neck and the central axis of the acetabulum. The second incision is a posterior incision approximately 2.5-3.75 centimeters (1-1.5 inches) positioned to be generally in axial alignment with the femoral shaft.

The femoral head is severed from the femoral shaft and removed through the anterior incision. The acetabular cup is placed in the acetabulum through the anterior incision, while the posterior incision is used to prepare the femoral shaft to receive a femoral stem. A femoral stem is inserted through the posterior incision and positioned in the femoral shaft. Procedures performed through the posterior incision may be observed through the anterior incision and vice versa.

For the purpose of the following discussion, a total hip arthroplasty is defined as a replacement of the femoral head with or without the use of a separate acetabular component. The specific designs which can be utilized in accordance with the present invention include a total hip replacement and a bipolar or monopolar endo prosthesis. The technique is suitable for cemented or cementless anchorage of the components.

The invention, in one form thereof, comprises a method of performing a total hip arthroplasty. The method of this form of the current invention includes the steps of: making an anterior incision, making a posterior incision, preparing an acetabulum to receive an acetabular cup through the anterior incision, seating an acetabular cup in the acetabulum through the anterior incision, preparing a femur to receive a femoral stem, and seating the femoral stem in the femur.

The invention, in another form thereof, comprises a method of performing a total hip arthroplasty. The method of this form of the current invention includes the steps of: preparing a femur to receive a femoral stem, placing a protective bag over the femoral stem, and seating the femoral stem in the femur.

The invention, in another form thereof, comprises a method of performing a total hip arthroplasty. The method of this form of the current invention includes the steps of: placing the patient in supine position; palpating the femoral neck and making an anterior incision of about 3.75-5 centimeters (1.5-2 inches) in line with the femoral neck and the central axis of the acetabulum; performing a blunt dissection of the muscle exposed by the anterior incision to expose the capsule of the hip joint; incising the capsule of the hip joint; retracting a portion of the capsule to visually expose the femoral neck; utilizing an osteotomy guide to mark a cut path along which a cut will be made to remove the femoral head and a portion of the femoral neck; cutting along the cut path; incising the ligamentum teres femoris; in situ morselizing the cut away femoral head and neck as necessary for removal through the anterior incision; removing the morsels of the femoral neck and head through the anterior incision; reaming the acetabulum; seating the appropriate acetabular cup in the reamed acetabulum; inserting a curved awl having a substantially straight distal end into the anterior incision; aligning the distal end of the awl with the femoral axis; palpating the distal end of the awl and making a posterior incision having a length of about 2.5-3.75 centimeters (1-1.5 inches) at the location of the distal end of the awl; performing a blunt dissection to provide an access through the posterior incision to the femoral shaft; threading a retractor into the recess formed between the posterior incision and the femoral shaft; passing a guide wire through the retractor and into the cancellous bone of the femoral shaft; positioning the guide wire in the cannula of a femoral reamer; reaming the femoral shaft with the femoral reamer using the guide wire to locate the cancellous bone of the femur; observing the reaming activity through the anterior incision; removing the femoral reamer; utilizing the guide wire to guide a rasp to the femoral shaft; positioning the rasp in the femoral shaft while observing through the anterior incision; removing the guide wire; removing the retractor from the posterior incision; positioning a trial acetabular liner in the acetabular cup through the anterior incision; affixing a provisional neck to the rasp through the anterior incision; affixing a provisional head to the provisional neck through the anterior incision; performing a trial reduction with the trial acetabular liner, provisional neck and provisional head in place; dislocating the provisional head; removing the trial acetabular liner through the anterior incision; removing the provisional neck and head through the anterior incision; removing the rasp through the posterior incision; seating a final acetabular liner in the acetabular cup through the anterior incision; inserting a femoral implant through the posterior incision; inserting a final femoral head through the anterior incision; affixing the final femoral head to the femoral implant; reducing the hip; and closing the incisions.

In one form of the current invention, the step of positioning a rasp in the femoral shaft comprises: locking the rasp to a rasp handle having a cannular insertion member with a distal rasp engagement guide and an elongate aperture sized to accommodate a flexible cable, an engagement slot for selectively engaging an end of the flexible cable, a selectively actuatable grip operable to tension the flexible cable, a lock for selectively locking the grip in a position to tension the flexible cable, and an impact surface for receiving blows to place or remove the rasp; positioning the guide wire in a cannula of the rasp and the cannula of the rasp handle; guiding the rasp and the cannular insertion member through the posterior retractor to a proximal end of the femoral shaft using the guide wire; striking the impact surface to position the rasp within the femoral shaft; unlocking the grip; releasing the flexible cable from the engagement slot; and removing the rasp handle.

In one form of the current invention, the step of locking the rasp to a rasp handle comprises: engaging a distal end of the flexible cable in the rasp; inserting the flexible cable through the elongate aperture of the rasp handle; guiding the distal rasp engagement guide into a rasp engagement guide receiving portion on the rasp; engaging the proximal end of the flexible cable in the engagement slot; and tensioning the flexible cable.

In one form of the current invention, the step of removing the rasp from the femoral shaft comprises: reinserting the flexible cable through the elongate aperture of the cannular insertion member (the flexible cable remains engaged with the rasp placed in the femur and protrudes from the posterior wound); reinserting the cannular insertion member through the posterior retractor; guiding the distal rasp engagement guide into the rasp engagement receiving portion on the rasp; engaging the proximal end of the flexible cable in the engagement slot; tensioning the flexible cable; and impacting the impact surface to remove the rasp from the femoral shaft.

The invention, in another form thereof, comprises a method of removing a femoral neck and head. The method of this form of the current invention includes the steps of: making an anterior incision in line with the femoral neck; providing an osteotomy guide having a handle and with an alignment portion and a cut guide affixed to the handle; aligning the alignment portion with the femoral axis, marking a cut path defined by the cut guide, and cutting along the cut path to remove a cut portion comprising a portion of the femoral neck and the femoral head.

The invention, in another form thereof, comprises a method of making a posterior incision aligned with a longitudinal axis of the femur. The method of this form of the current invention includes the steps of making an anterior incision aligned with the femoral neck, providing an awl having a handle and a curved awl shaft having a distal end, aligning the distal end with the longitudinal axis of the femur, palpating a location of the distal end of the awl, and making a posterior incision at the location of the distal end of the awl.

The invention, in another form thereof, comprises a method of preparing a femur to receive a femoral implant. The method of this form of the current invention includes the steps of: removing the femoral head and neck as necessary, making a posterior incision of approximately 2.5-3.75 cm which is substantially aligned with the central axis of the femoral shaft, performing a blunt dissection to provide an access through the posterior incision to expose the femoral shaft, inserting a retractor comprising a tunnel sized for insertion through the access into the access, and preparing the femur to receive a femoral implant through the retractor.

The invention, in another form thereof, comprises an osteotomy guide having a handle allowing use of the osteotomy guide a distance from a femur as well as an alignment portion and a cut guide affixed to the handle.

The invention, in another form thereof, comprises an awl having a handle and an awl shaft with a distal end. The distal end of the awl shaft is adapted to be inserted into an anterior incision and aligned with the longitudinal axis of a femur to locate a posterior incision operable to expose a proximal end of the femur.

The invention, in another form thereof, comprises a retractor formed of a tunnel sized for insertion through an access leading to the femoral shaft in a body.

The invention, in another form thereof, comprises a rasp handle having an insertion member with engagement means for selectively engaging a cable which is affixable to a rasp. In one form of the current invention, the engagement means comprises an engagement slot for selectively engaging the cable.

The invention, in another form thereof, comprises a provisional femoral neck apparatus including a provisional femoral neck having a hollow, substantially cylindrical body. A spring biased locking piston is provided and housed within said hollow cylindrical body. The locking piston includes a tapered body portion. Application of a radial force to the tapered body portion moves the locking piston against the biasing force of the spring. The blades of a forceps may be utilized to apply the radial force to the tapered portion of the locking piston.

The invention, in another form thereof, comprises a provisional prosthetic femoral neck having a guide surface and a provisional femoral stem including a mate to the guide surface. The guide surface is piloted to the mate to join the femoral neck and the femoral stem. In one form of the current invention, the femoral neck is substantially cylindrical and is piloted to the femoral stem in a radial direction.

The apparatus and method of the current invention advantageously allow a total hip arthroplasty to be performed in a minimally invasive way, which hastens patient recovery.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is a side elevational view of a patient illustrating a pair of incisions made according to the current invention as well as the incision utilized in prior art procedures;

FIG. 2 is an anterior elevational view of a hip joint illustrating the femoral neck axis;

FIG. 4 is an anterior elevational view of the femoral neck with an osteotomy guide of one form of the current invention operably positioned to designate a cut line thereon;

FIG. 6 is an anterior elevational view illustrating the femoral head and neck severed along the cut line indicated by the osteotomy guide;

FIG. 7 is an anterior elevational view illustrating the removal of a portion of the femoral head and neck;

FIG. 9 is a side elevational view of an acetabular cup inserter relative to a patient lying in the supine position;

FIG. 10 is an anterior elevational view of a portion of the cup inserter illustrated in FIG. 9 and a patient lying in the supine position;

FIG. 14 is a perspective, exploded view of one embodiment of a tubular retractor in accordance with the present invention;

FIG. 14A is a side elevational view of an alternative embodiment of the tubular retractor;

FIG. 15 is a perspective view illustrating the insertion of a guide wire into the tubular retractor;

FIG. 16 is a perspective view illustrating reaming of the femoral shaft;

FIG. 17A is a perspective view of an end cutter;

FIG. 17B is a perspective view of a femoral reamer;

FIG. 18 is a side elevational, partial sectional view of an end cutter inserted into a tubular retractor of the present invention;

FIG. 19A is a perspective view illustrating an inserted rasp, with the rasp handle removed, and with the cable used to affix the rasp to the rasp handle protruding from the posterior incision;

FIGS. 20A and 20B are partial sectional views of the rasp handle;

FIG. 21 is an exploded view of the rasp handle and a rasp to be connected thereto;

FIG. 21A is a partial elevational view along line 21A-21A of FIG. 21;

FIG. 23 is a perspective view of the provisional neck and mating forceps of the present invention;

FIG. 24A is a partial sectional, radial elevational view of the provisional neck;

FIGS. 24B and 24C are radial elevational views thereof;

FIG. 30 is a perspective view of a hip prosthesis which can be implanted according to the method of the current invention.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 2A:
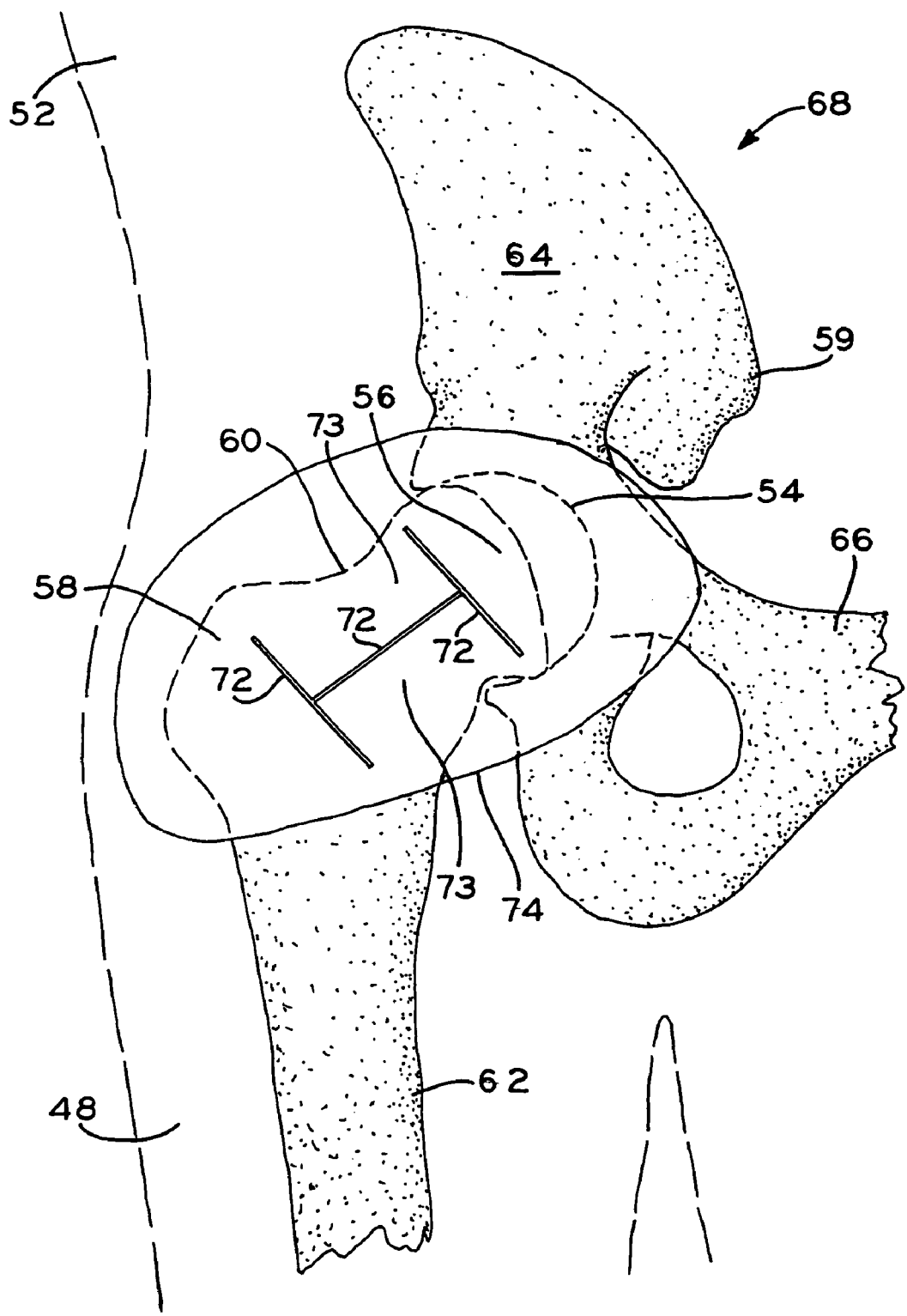
FIG. 2A is an anterior elevational view illustrating the capsule of the hip joint.

A total hip arthroplasty can be performed, according to the teachings of the current invention through two incisions, each no more than 5 centimeters (2 inches) in length. An anterior incision is made along the axis of the femoral neck, while a posterior incision is made generally in axial alignment with the femoral shaft. Referring to FIG. 1, a partial illustration of a patient 40 including torso 52, buttock 50, and leg 48 illustrates prior art incision 42 as well as anterior incision 44 and posterior incision 46 of the current invention. Prior art incision 42 is approximately 25 centimeters (10 inches) long, while anterior incision 44 and posterior incision 46 are each no more than 5 centimeters (2 inches) in length.

According to the method of total hip arthroplasty of the current invention, patient 40 is initially placed in a supine position on an operating table. Either a standard operating table or, alternatively, a radiolucent Jackson table is used. A radiolucent Jackson table is preferred if the surgical team intends to use intraoperative image intensification. In one exemplary embodiment, a Storz viewsite endoscopic system can be used. A Storz viewsite endoscopic system provides a sterile viewing screen for endoscopic images. The sterile viewing screen of a Storz viewsite endoscopic system can be positioned within the surgical field immediately adjacent to anterior incision 44. Other known endoscopic systems may further be utilized during the total hip arthroplasty of the present invention. Referring now to FIG. 2, with ipsilateral leg 48 in a neutral position, two prominent bony landmarks are palpated, the anterior superior iliac spine (ASIS) 59 and the greater trochanter 58 of femur 62. Ilium 64 and pubis 66 of hip 68 are shown to better illustrate the relevant area of the body. In one exemplary embodiment, the approximate anterior incision starting point 71 is identified two fingerbreadths inferior and two fingerbreadths anterior to the tubercle of the greater trochanter 58. The approximate finish point for the anterior incision is identified three fingerbreadths inferior and two fingerbreadths lateral to the anterior superior iliac spine (ASIS) 59. In another exemplary embodiment, the approximate anterior incision starting point 71 is identified 3-4 centimeters inferior and 2 centimeters lateral to ASIS 59. Having identified starting point 71 3-4 centimeters inferior and 2 centimeters lateral to ASIS 59, the path of anterior incision 44 is extended obliquely from starting point 71 toward the prominence of greater trochanter 58 along the axis of femoral neck 60. With the use of a spinal needle, the appropriate starting point 71 and the path of the anterior incision are identified by impaling the skin down to bone to confirm the central axis 70 of femoral neck 60.

An oblique incision of approximately 3.75-5 centimeters (1.5-2 inches) is made from the starting site 71 toward the prominence of the greater trochanter along the axis 70 of the femoral neck 60 and the central axis of acetabulum 54. The incision is extended along the same plane through subcutaneous tissues, exposing the underlying fascia lata. The internervous plane between the tensor fascia lata muscle and the sartorius is identified by palpation and developed by curved scissors and blunt dissection. The sartorius can be made more prominent by externally rotating the leg to apply tension on the muscle. Deep to the tensor fascia lata and the sartorius is an internervous interval between the rectus femoris and the gluteus medius. This plane is developed by blunt dissection. A lateral retraction of the tensor fascia lata permits a visualization of the capsule 74 of the hip joint as illustrated in FIG. 2A.

Figure 3:
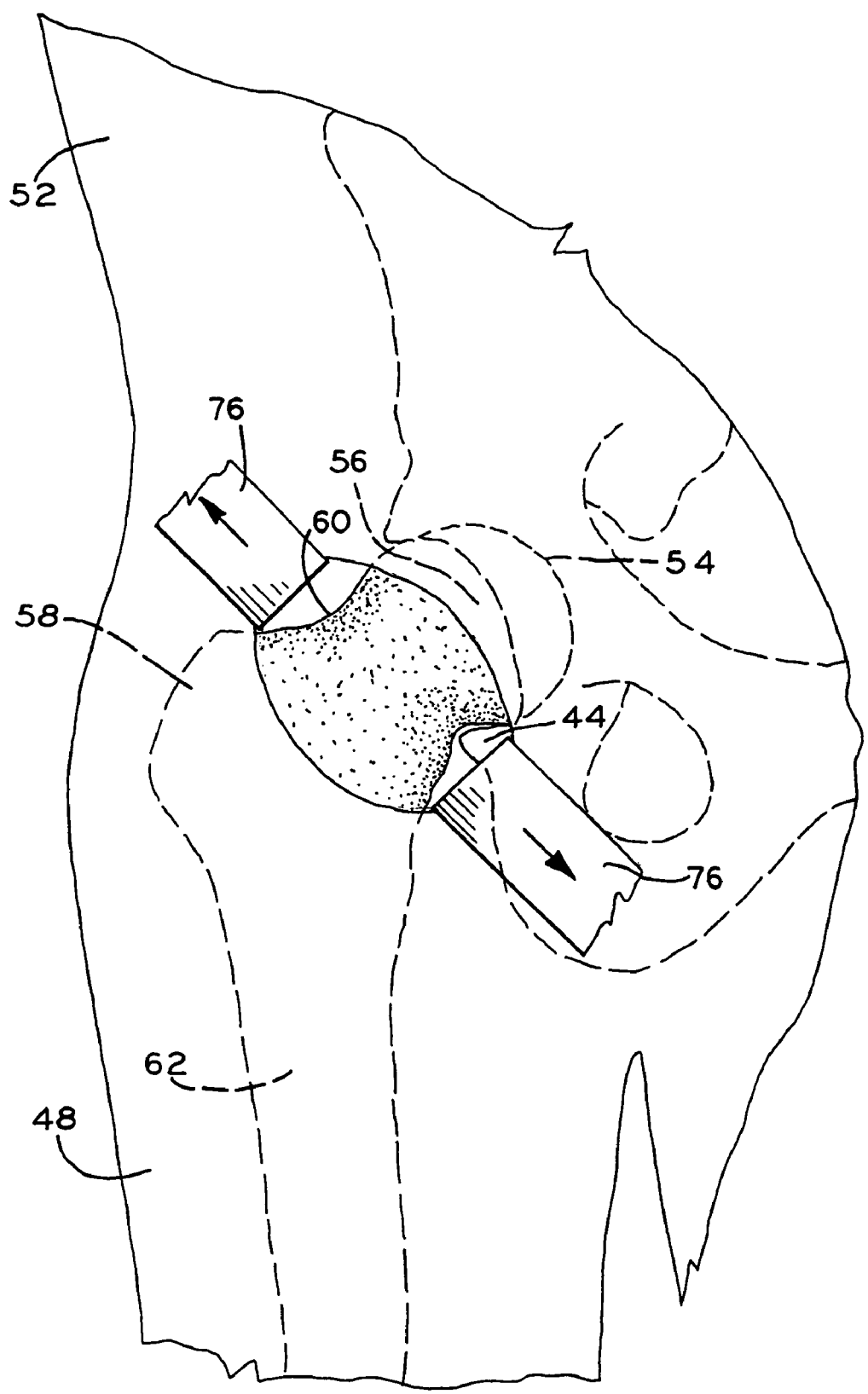
FIG. 3 is an anterior elevational view of the femoral neck exposed by incising the hip capsule.

Leg 48 is externally rotated to create tension on capsule 74. Capsule 74 is incised along the axis 70 (FIG. 2) of femoral neck 60 from the equator of femoral head 56 to the intertrochanteric ridge on the femur 62. The capsular incision takes the form of an "H-shaped" window formed by incisions 72. The H-shaped window is formed by adding supplementary perpendicular limbs around the equator of the femoral head 56 and the base of the femoral neck 60 to the initial incision along the axis 70 of femoral neck 60. As a form of retraction, heavy sutures are used to provisionally attach the capsular flaps 73 to the subcutaneous tissues. As illustrated in FIG. 3, retractors 76 are placed inside capsular flaps 73 and underneath the superior and inferior borders of femoral neck 60 to expose the entire length of femoral neck 60 from the inferior aspect of femoral head 56 to the intertrochanteric ridge. Retractors 76 can be, e.g., Cobra retractors. In one exemplary embodiment, each retractor houses a light source and can also serve to anchor an endoscope. Retractors 76 thereby provide continuous visualization and illumination of the wound. In one exemplary embodiment, JAKOSCOPE retractors having integral fiberoptic light sources are utilized in accordance with present inventions.

Referring now to FIG. 4, a femoral cutting tool 86, e.g., an oscillating saw or a power burr is used to excise femoral neck 60. A custom osteotomy guide 78 is placed through anterior incision 44 (FIG. 1) and functions to guide the femoral neck cut. Alignment portion 82 of osteotomy guide 78 is aligned with the longitudinal axis of femur 62, while cut guide 84 is positioned on femoral neck 60. Handle 80 of osteotomy guide 78 facilitates positioning and repositioning of osteotomy guide 78 through anterior incision 44. After placement of osteotomy guide 78, cut line 85 is scored as is known in the art. Osteotomy guide 78 is thereafter removed through anterior incision 44 and femoral cutting tool 86 is inserted through anterior incision 44 and utilized to cut along cut line 85 and displace portion 88 (FIG. 6) from femur 62.

Retractors 76 are repositioned around the anterior and posterior rims of the acetabulum. A custom curved cutting tool. (i.e., the "ligamentum teres cutter") is passed behind femoral head 56 to sharply incise the ligamentum teres, thus mobilizing cut portion 88 as illustrated in FIG. 6. Cut portion 88 includes femoral head 56 as well as a portion of femoral neck 60 (FIG. 4). Cut portion 88 is thereafter removed through anterior incision 44 with a custom femoral head bone grasper 94 (FIG. 7). If there is difficulty removing cut portion 88 in one piece, it may be in situ morselized using cutting tool 87 (FIG. 6), e.g., a power burr. Morsels 92 may then be removed through anterior incision 44. Morselizing of cut portion 88 is accomplished making cuts which substantially mirror the cuts in hip capsule 74. In one exemplary embodiment, a corkscrew and hip skid removes the entire femoral neck, as in hip fracture. Irrigation and suction devices can be used to cool the bone and facilitate the removal of bony debris in hip capsule 74. In one exemplary embodiment, a fiberoptic endoscope is placed into the hip joint to confirm the complete removal of bony debris.

Figure 8B:
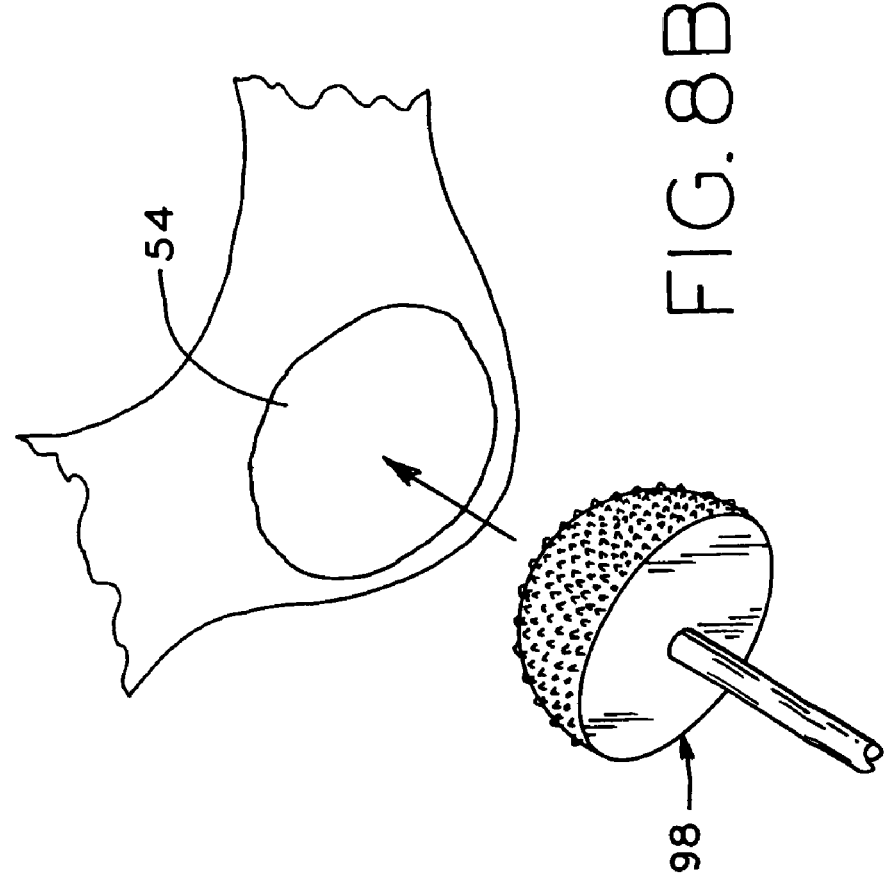
FIGS. 8A and 8B illustrate preparation of the acetabulum to receive the acetabular cup.
Figure 8A:
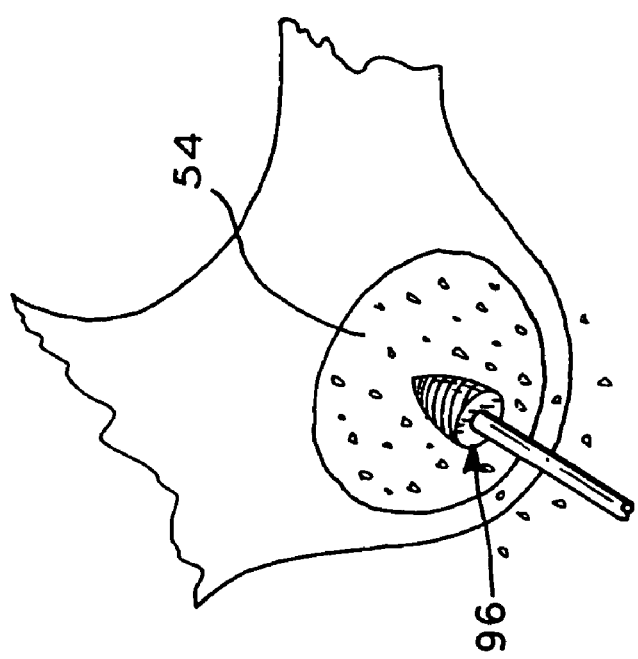

As illustrated in FIG. 8A, the fibro-fatty tissue within the cotyloid fossa of acetabulum 54 is removed with the use of, e.g., a high-speed acorn-tipped cutting tool 96, Rongeur forceps, and a curette. Thereafter, the acetabular labrum is trimmed with a scalpel. As illustrated in FIG. 8B, acetabulum 54 is then progressively reamed with standard acetabular reamer 98. Acetabular reamers within a predetermined size range are utilized until the optimal size of the acetabulum is reached. Sizing of the acetabulum is facilitated by the use of pre-operative templates and radiographs as is known in the art. Once again, an endoscope can be used to aid in visualization during the reaming process. Typically the acetabulum is under reamed by approximately 2 mm with respect to the diameter of the anticipated acetabular cup so as to create an interference fit. High speed acorn-shaped cutting tool 96, and acetabular reamer 98 enter the body through anterior incision 44.

After a trial fitting, a press-fit acetabular cup of the appropriate size is firmly seated with a standard cup inserter 100 as illustrated in FIG. 9 and impacted into the acetabular recess as is known in the art. Acceptable press fit acetabular cups include the ZIMMER HGP II or TRILOGY cups. Proper positioning of the acetabular cup is achieved with a custom anteflexion and pelvic alignment guide. Patient 40 is placed in supine position on operating table 102. Aligning rod 104 is aligned with the mid lateral axis of torso 52 while main shaft 105 is maintained approximately 30° from operating table 102 for proper seating of the acetabular cup. To augment fixation of the cup, a flexible drill can be used to guide the placement of one or more acetabular screws. In some cases, acetabular screws will not be necessary. The insertion of the acetabular liner is deferred until the proximal femur has been prepared for the insertion of a trial stem. As illustrated by the anterior elevational view of FIG. 10, patient 40 remains in the supine position on operating table 102 (FIG. 9) while cup inserter 100 is utilized to seat the acetabular cup.

For preparation of the femur, the patient is repositioned with a pad placed under the ipsilateral hip. The hip is slightly flexed, adducted approximately 30°, and maximally externally rotated. Retractors 76 are repositioned around the medial and lateral aspects of femur 62. Alternatively, a self-retaining retractor with a light source attachment and an endoscope holder can be positioned in anterior incision 44 to provide constant visualization and illumination of femur 62.

With a scalpel or curved osteotome, the soft tissues along the anterior surface of femur 62 just inferior to the intertrochanteric ridge are subperiosteally reflected to expose the bone for a width of approximately 1 cm. This sharp subperiosteal elevation continues superolaterally onto the anterior margin of the greater trochanter. Then with curved Mayo scissors a pathway is developed by blunt dissection that is directed superficially to the anterior fibers of the gluteus minimus towards buttock 50 (FIG. 11).

Figure 11:
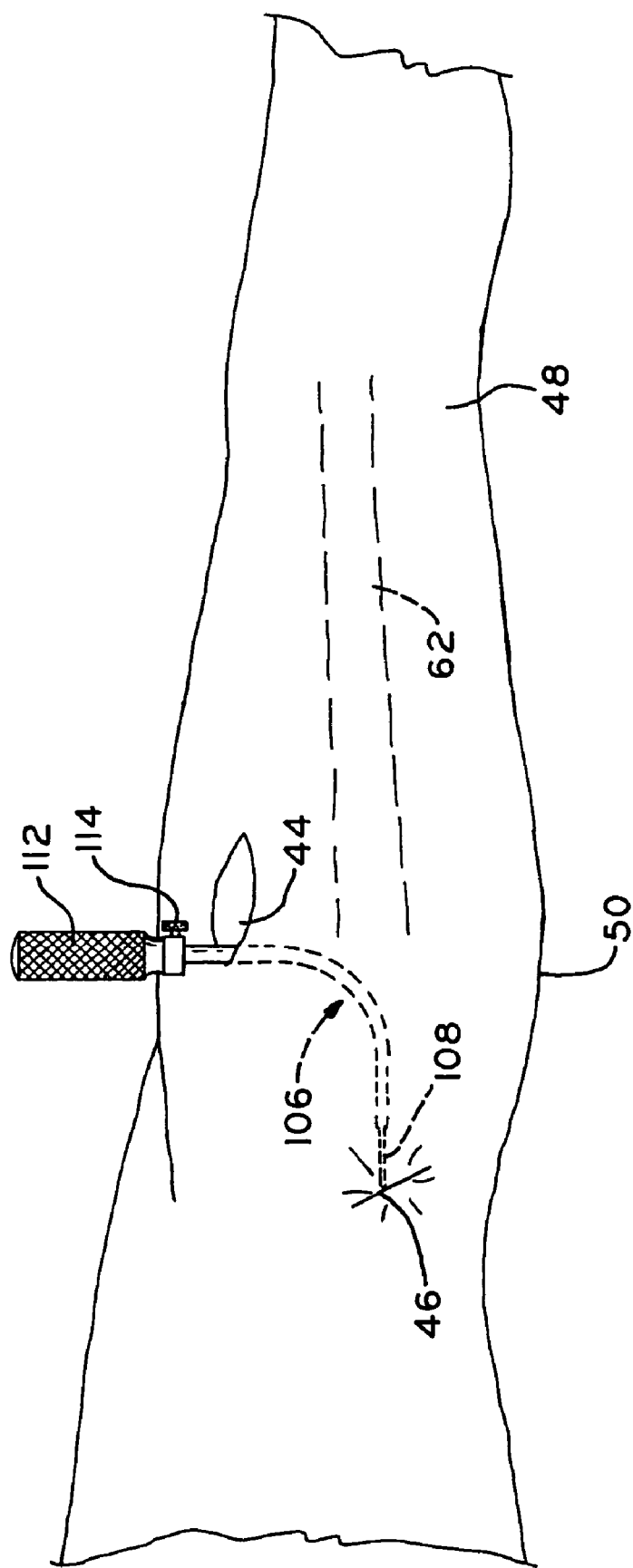
FIG. 11 is a side elevational view illustrating the use of a curved awl to locate a posterior incision.
Figure 13:
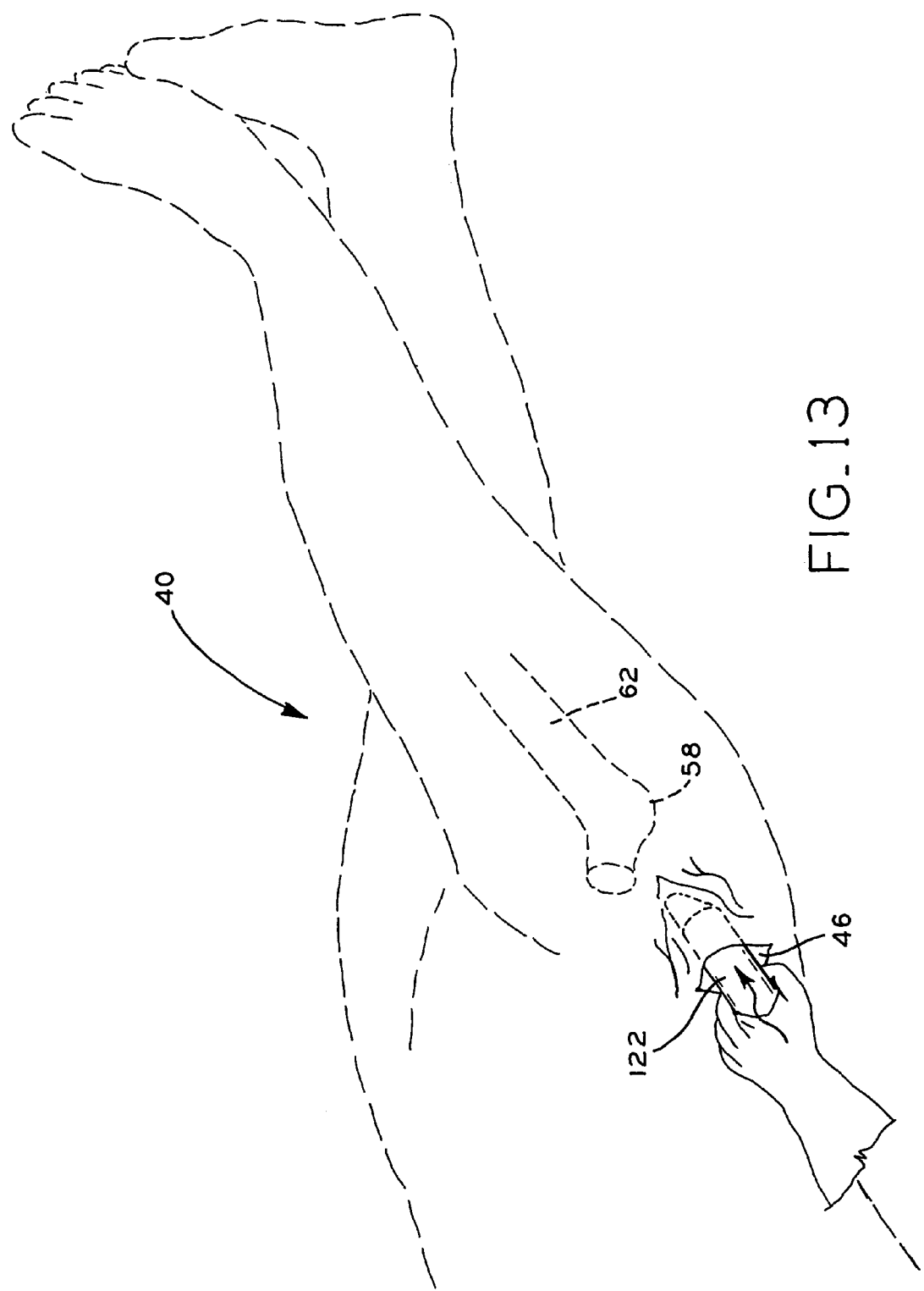
FIG. 13 is a perspective view illustrating the insertion of a posterior retractor in the posterior incision.

As illustrated in FIG. 11, awl 106 is inserted through the anterior incision 44, directed through the cleft between the gluteus medius and maximus in line with the shaft of the femur and piriformis fossae region, and advanced into the soft tissues of buttock 50 until its pointed distal end 108 can be palpated on the surface of the skin. Distal end 108 of awl 106 is generally aligned with the longitudinal axis of femur 62. At the point where distal end 108 is palpated, posterior incision 46 of approximately 2-3 cm (0.8-1.2 inches) is made and extended through the subcutaneous tissues and fascia lata to expose the underlying gluteus maximus. A tract to femur 62 is developed along the path created by awl 106. The gluteus maximus is split bluntly in line with its fibers with curved Mayo scissors. Finger dissection may be utilized to reach the posterior piriformis fossa region. Into this pathway, via posterior incision 46, custom elliptical posterior retractor 122, complete with its inner sleeves, is threaded (FIG. 13) down to the osteotomized femoral neck. In one exemplary embodiment, elliptical posterior retractor 122 includes posterior lip 128 (FIG. 14). In this embodiment, retractor 122 is threaded down to the osteotomized femoral neck until posterior lip 128 lies beneath the posterior intertrochanteric ridge. FIG. 14A illustrates an embodiment of rasp tunnel 130 without posterior lip 128. In an alternative embodiment, each component of posterior retractor 122 (i.e., guide tube 124, reamer tunnel 126, and rasp tunnel 130) is individually inserted and removed as necessary. In an embodiment in which guide tube 124, reamer tunnel 126, and rasp tunnel 130 are individually inserted and removed into posterior incision 46, each individual tunnel may be provided with a posterior lip similar to posterior lip 128 illustrated in FIG. 14. Rasping and reaming of the femur will now be described. The posterior capsule will be entered to facilitate rasping and reaming of the femur.

Referring now to FIG. 15, blunt tipped guide wire 146 is inserted through guide tube 124 of posterior retractor 122 and advanced into femoral canal 148. While FIG. 15 illustrates guide tube 124 nested in reamer tunnel 126 and rasp tunnel 130, guide tube 124 may be directly inserted through posterior incision 46. If the cancellous bone of femur 62 is too dense to permit insertion of blunt tipped guide wire 146, then a conical cannulated reamer or end mill is used to prepare the femoral metaphysis. If a nested posterior retractor configuration is utilized, guide tube 124 must be removed so that the reamer can be inserted through reamer tunnel 126 of posterior retractor 122. Similarly, if a nested configuration is not utilized, reamer tunnel 126 must be inserted into posterior incision 46. In any event, blunt tipped guide wire 146 is inserted about halfway down femoral canal 148. The following detailed description of the invention makes reference to a nested posterior retractor configuration. It will be understood by those skilled in the art that if the nested configuration is not utilized, each individual component of posterior retractor 122 will be inserted and removed through posterior incision 46 as necessary.

Figure 19:
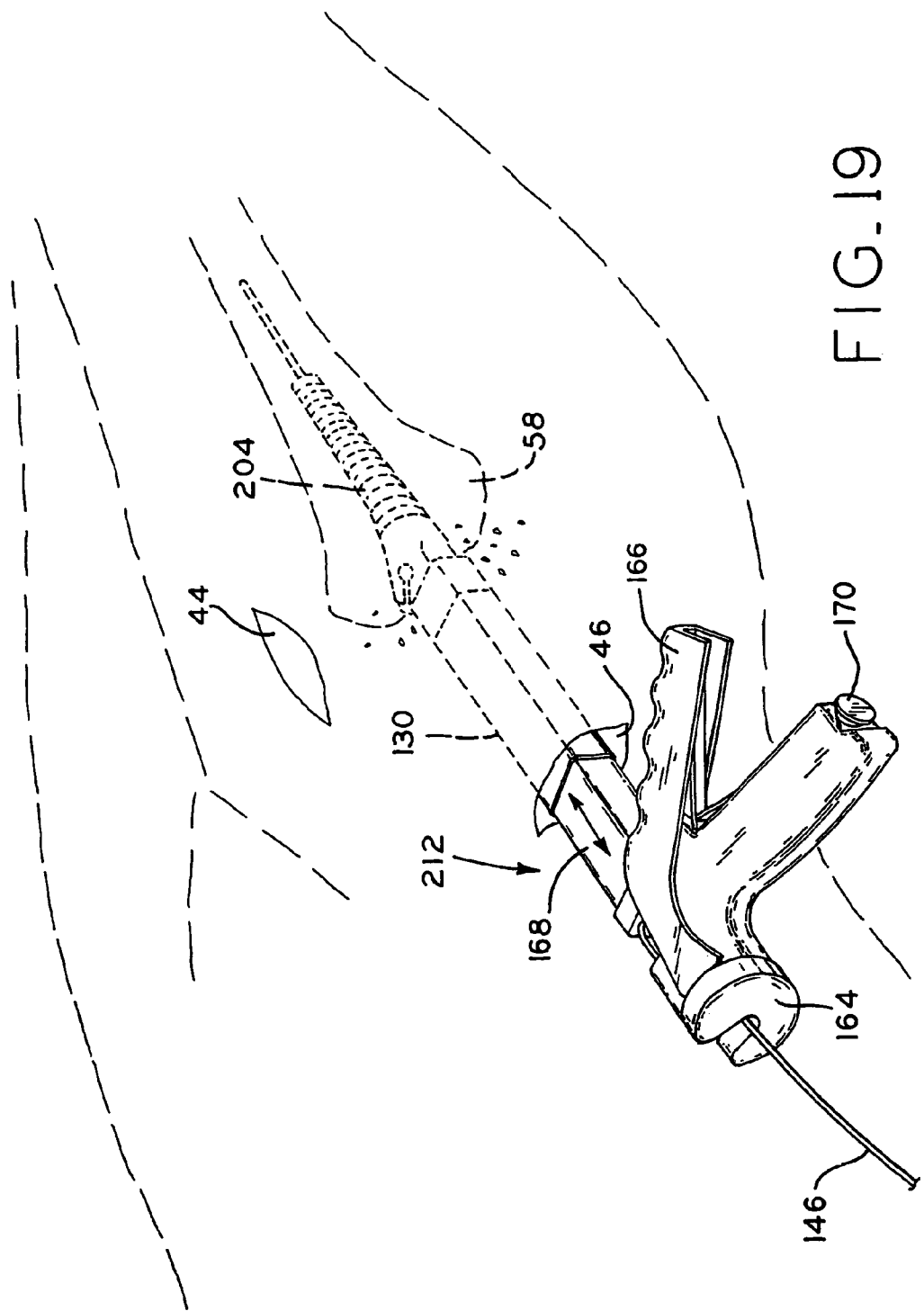
FIG. 19 is a perspective view of a rasp handle after inserting a rasp into the femoral shaft.

FIG. 16 illustrates preparation of femoral canal 148 to receive rasp 204 (FIG. 19). Guide tube 124 is removed from posterior retractor 122 and end cutter 150 (FIG. 17A) is inserted through reamer tunnel 126. FIG. 18 illustrates end cutter 150 positioned within reamer tunnel 126. End cutter 150 includes elongate aperture 160 through which guide wire 146 passes and guides end cutter 150. End cutter 150 is actuated by any of the many actuating devices known in the art. After end cutting is complete, end cutter 150 is removed through reamer tunnel 126 and reamer 151 (FIG. 17B) is inserted therethrough. Reamer 151 includes reamer guide aperture 161 through which guide wire 146 passes and guides reamer 151 as it reams femoral canal 148. Reamers of progressive increase in their outer diameter are sequentially placed over guide wire 146 and femoral canal 148 is reamed until cortical "chatter" is felt. As is known in the art, the optimal diameter of femoral canal 148 is provisionally determined by preoperative templating. Some surgeons may choose to avoid reaming of the femoral shaft and instead utilize a broach as is known in the art. A broach may be inserted in accordance with the current invention as described hereinbelow with respect to rasp insertion.

After the correct diameter of femoral canal 148 is reamed out, reamer tunnel 126 (FIG. 14) is removed from posterior retractor 122 so that rasp 204 and rasp handle 212 (FIG. 19) can be inserted over guide wire 146 to complete preparation of femur 62. Guide wire 146 is inserted into rasp guide aperture 214 and rasp handle guide aperture 202 to guide rasp 204 to prepared femur 62. Impact surface 164 is struck, as is known in the art, to place rasp 204 in femur 62. While rasp 204 is being impacted, the rotational alignment can be assessed by direct visual scrutiny of femur 62 through anterior incision 44. Furthermore, assessment of the alignment of rasp handle 212 with respect to the patella, lower leg, and foot facilitates alignment. On the normal proximal femoral metaphysis, a flattened area of anterior bone provides a highly reproducable landmark for the rotational alignment. This may not be true if the patient has experienced prior surgery or trauma.

Progressively larger rasps are inserted to achieve the optimal fit and fill in femur 62. Once the final rasp is fully seated, rasp handle 212 is removed along with guide wire 146 and posterior retractor 122, leaving distal end 208 of flexible cable 192 (FIG. 19A) attached to the proximal end of rasp 204 and proximal end 194 of flexible cable 192 protruding from posterior incision 46. The operation of rasp handle 212 will be further explained below.

Figure 22:
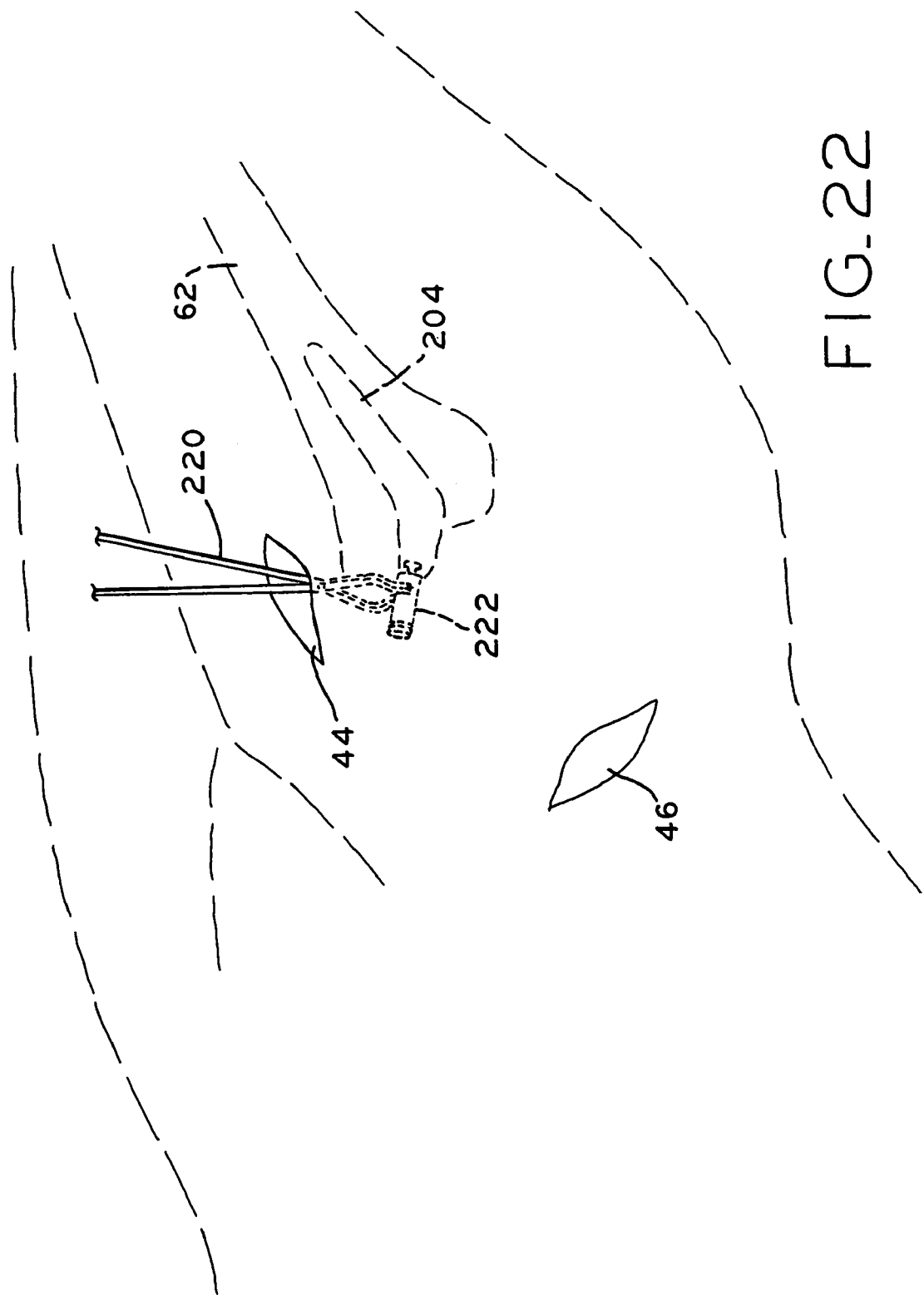
FIG. 22 is a perspective view illustrating placement of a provisional neck of the present invention.

After the final rasp is seated in femoral canal 148, a trial acetabular liner is placed through anterior incision 44 and into the seated acetabular cup with the use of a liner inserter as is known in the art. Provisional neck 222 is inserted through anterior incision 44 and locked to the top end of the seated rasp, as illustrated in FIG. 22. A trial femoral head is placed on the Morse taper of provisional neck 222 through anterior incision 44. The hip joint is reduced for an assessment of stability of the hip joint and limb length. Where necessary, a second assessment is made. Once the trial reduction is satisfactorily completed, the hip is dislocated and the provisional head and provisional neck 222 are removed. Rasp handle 212 is reinserted through posterior incision 46 over the free end of flexible cable 192. Rasp handle 212 is advanced until it can be locked with the seated rasp so that impact surface 164 can be impacted and the entire tool (i.e., rasp 204 and rasp handle 212) can be removed. The trial acetabular liner is removed through anterior incision 44. In an alternative embodiment, a trial reduction can be performed utilizing the final femoral implant and a trial femoral head.

Figure 25:
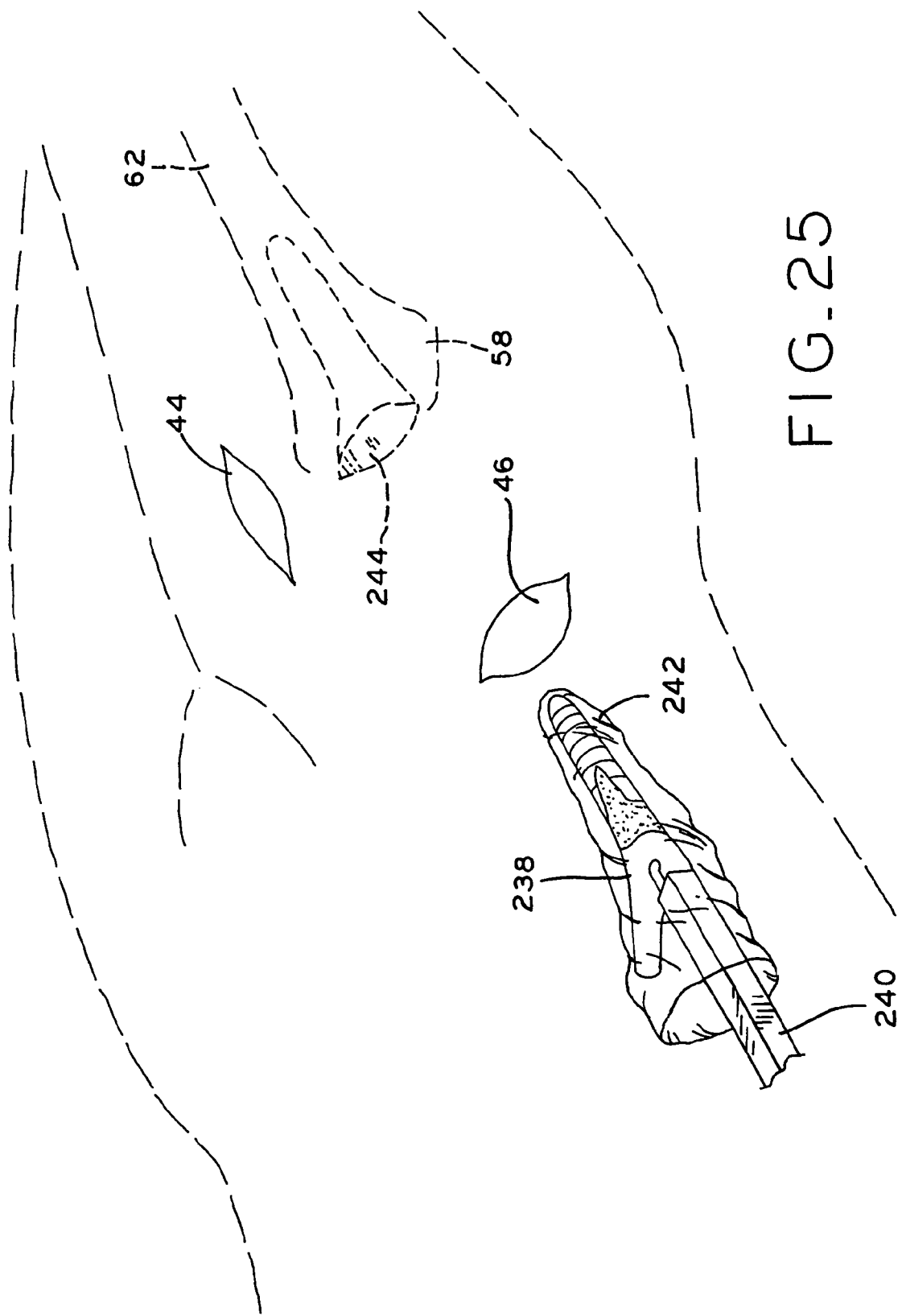
FIG. 25 is a perspective view illustrating the insertion of a femoral stem with a protective bag through the posterior incision.
Figure 29:
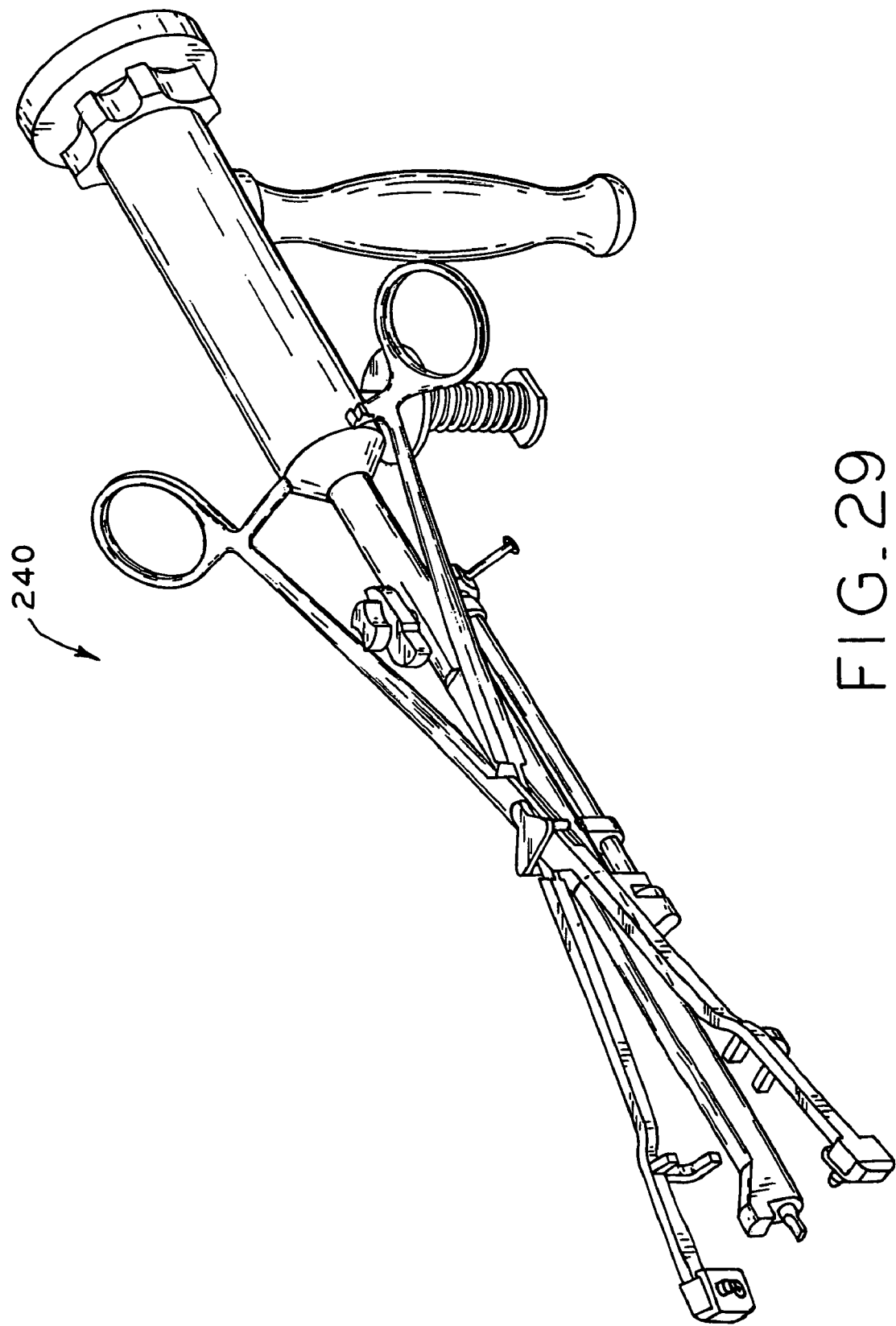
FIG. 29 is a perspective view of a femoral stem insertion tool in accordance with the teachings of the present invention.

Via anterior incision 44, the final acetabular liner 252 (FIG. 30) is seated into acetabular cup 250 (FIG. 30) with a liner inserter that permits its impaction in place, as is known in the art. Femoral implant 238 (FIG. 30) is anchored to femoral stem insertion tool 240 (FIG. 29) and placed through posterior incision 46. Femoral implant 238 can be, e.g., a VERSYS fiber metal taper, or a VERSYS fiber metal midcoat available from Zimmer, Inc. As illustrated in FIG. 25, femoral implant 238 is placed in protective, disposable bag 242 prior to its introduction into posterior incision 46. Protective, disposable bag 242 keeps femoral implant 238 clean as it is inserted through posterior incision 46. Note that FIG. 25 illustrates femoral implant 238 oriented as it will be when placed in femur 62. To insert femoral implant 238 through posterior incision 46, femoral implant 238 must be rotated 180° from this position to prevent impingement on the body. Femoral implant 238 is then rotated 180° after being completely inserted through posterior incision 46.

Figure 26:
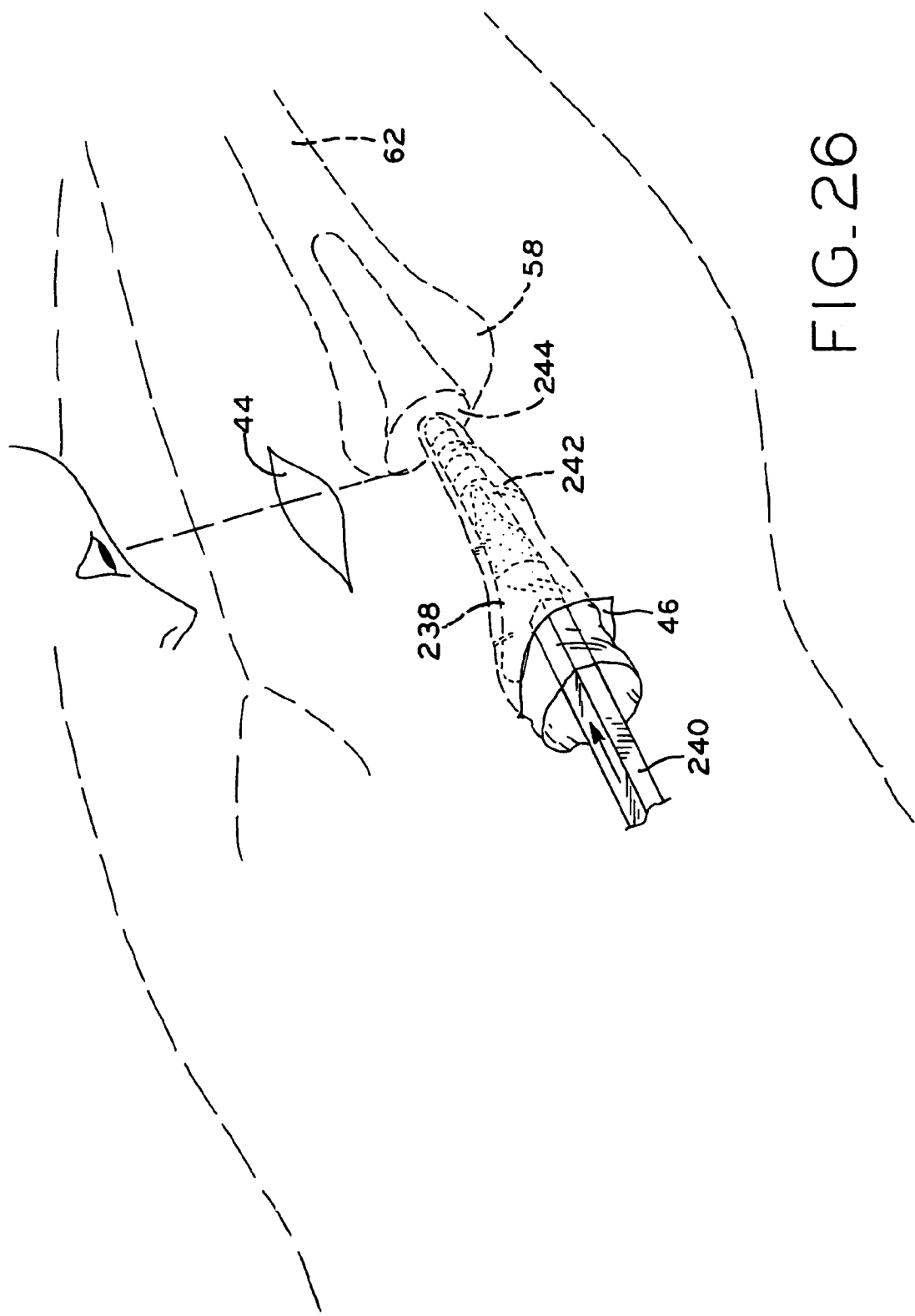
FIG. 26 is a perspective view illustrating alignment of the femoral stem while observing through the anterior incision.
Figure 27:
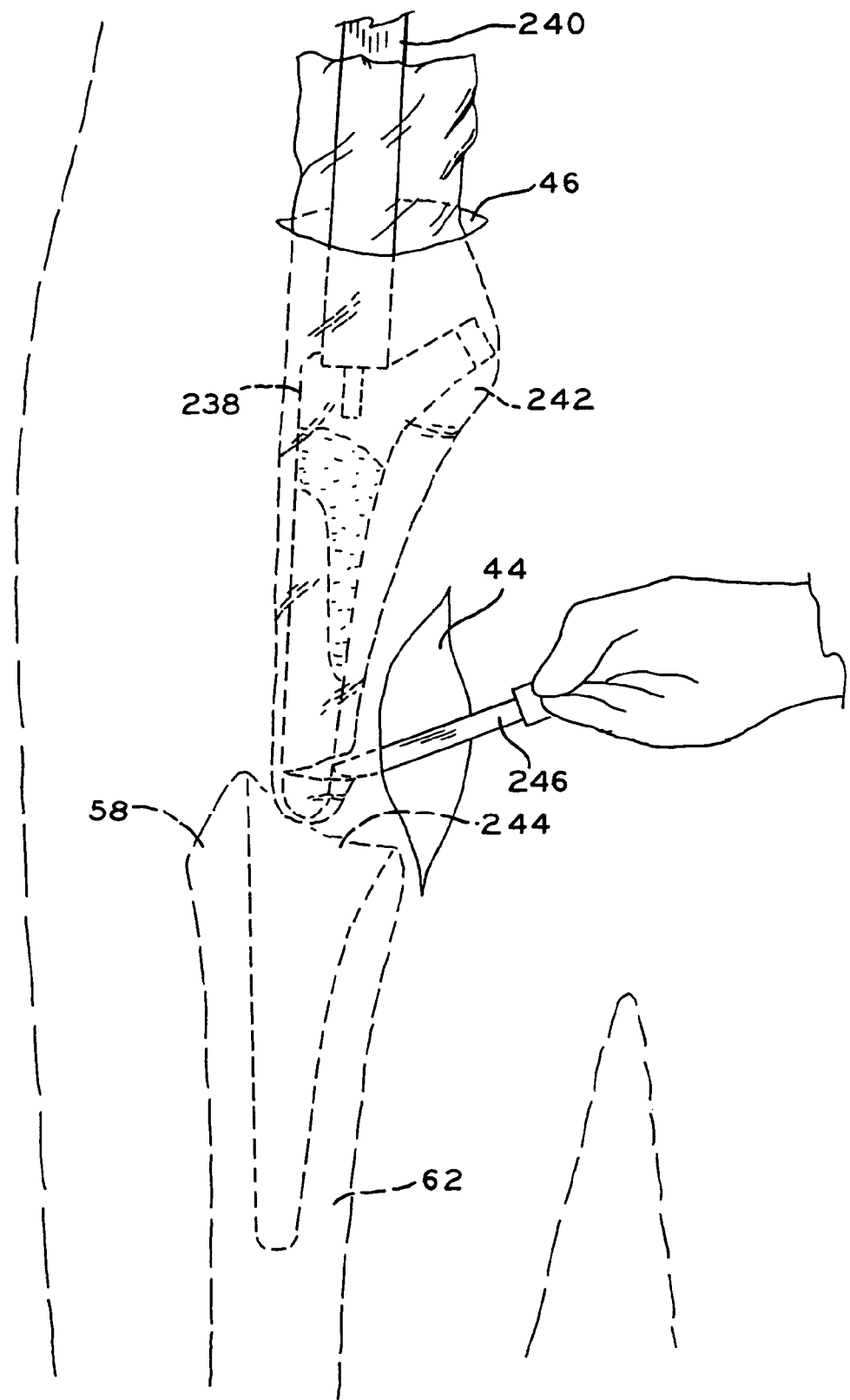
FIG. 27 illustrates an incision into the femoral stem protective bag prior to insertion of the femoral stem into the femoral shaft.
Figure 28:
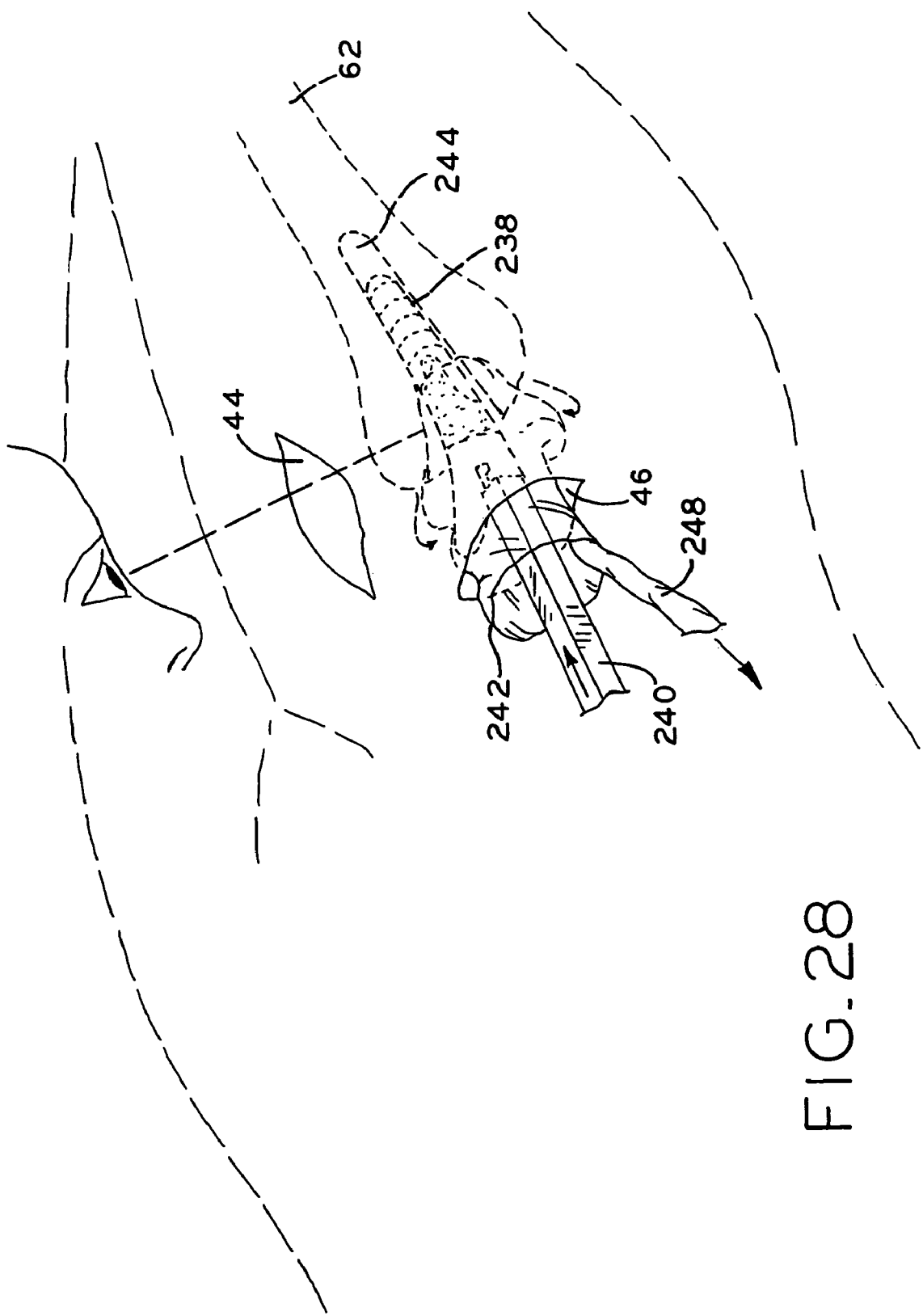
FIG. 28 is a perspective view illustrating removal of the femoral stem protective bag while inserting the femoral stem, with observation through the anterior incision.

FIG. 26 illustrates femoral stem 238 and bag 242 inserted through posterior incision 46. When the tip of femoral stem 238 approaches the osteotomized femoral neck, the distal end of bag 242 is incised as illustrated in FIG. 27. Scalpel 246 is inserted into anterior incision 44 to incise bag 242. As femoral stem 238 is driven into femoral canal 148, bag 242 is progressively removed through posterior incision 46 as illustrated in FIG. 28. After femoral stem 238 is fully seated, femoral stem insertion tool 240 (FIG. 29) is removed through posterior incision 46. Through anterior incision 44, the final femoral head is positioned on the femoral neck Morse taper using a standard holding device and secured with a standard impaction tool and mallet. The hip is then reduced and assessed for stability.

After appropriate antibiotic irrigation and pulsatile lavage, the hip capsule and the soft tissues are repaired with heavy sutures or staples. A suitable local anesthetic solution is injected into the closed hip joint as well as the capsular layer and the subcutaneous tissues, allowing superior postoperative pain relief. The fascial layers, subcutaneous tissues, and skin of both anterior and posterior wounds are closed in a conventional method and dressings are applied. A suction drain may be used at the discretion of the surgeon.

Figure 5A:
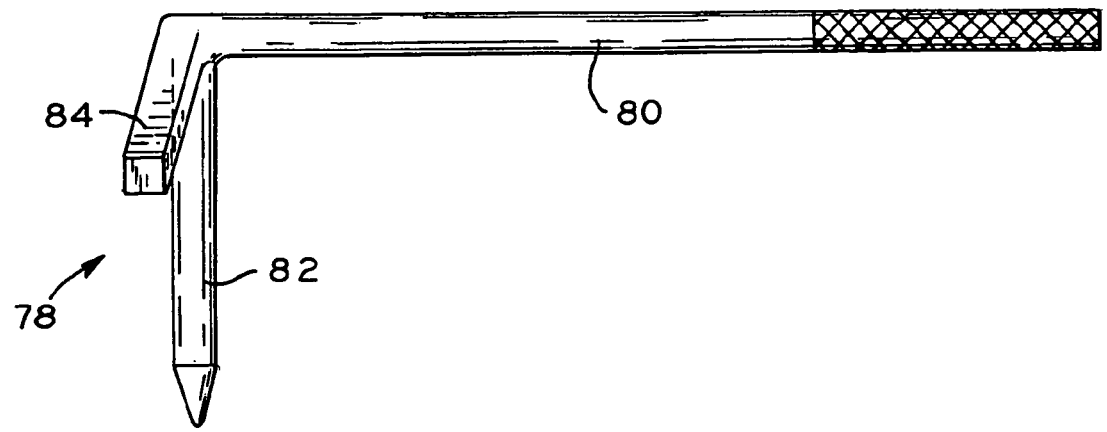
FIG. 5A is a side elevational view of an alternative embodiment of an osteotomy guide in accordance with the present invention.
Figure 5B:
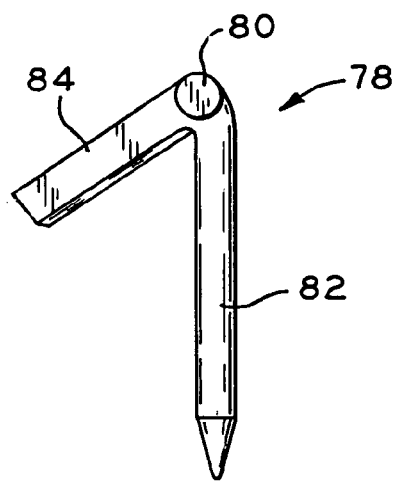
FIG. 5B is an elevational view thereof taken along the longitudinal axis of the handle.

Osteotomy guide 78, illustrated in use in FIG. 4, includes handle 80, alignment portion 82, and cut guide 84. In one exemplary embodiment, cut guide 84 and alignment portion 82 form a 60° angle. In one exemplary embodiment, alignment portion 82 includes a tapered distal end as illustrated in FIGS. 5A and 5B. Osteotomy guide 78 is inserted through anterior incision 44 and is positioned with alignment portion 82 being placed on femur 62 so that alignment portion 82 generally aligns with the longitudinal axis of femur 62. Handle 80 protrudes through anterior incision 44 and may be utilized to position osteotomy guide 78. After osteotomy guide 78 is properly positioned, cut guide 84 is utilized to mark cut line 85 on femoral neck 60 as illustrated in FIG. 4. Osteotomy guide 78 can be formed to function on either side of the body. FIG. 4 illustrates an osteotomy guide designed to function on the right femur, while FIG. 5B illustrates an osteotomy guide operable to function on the left femur.

Figure 12:
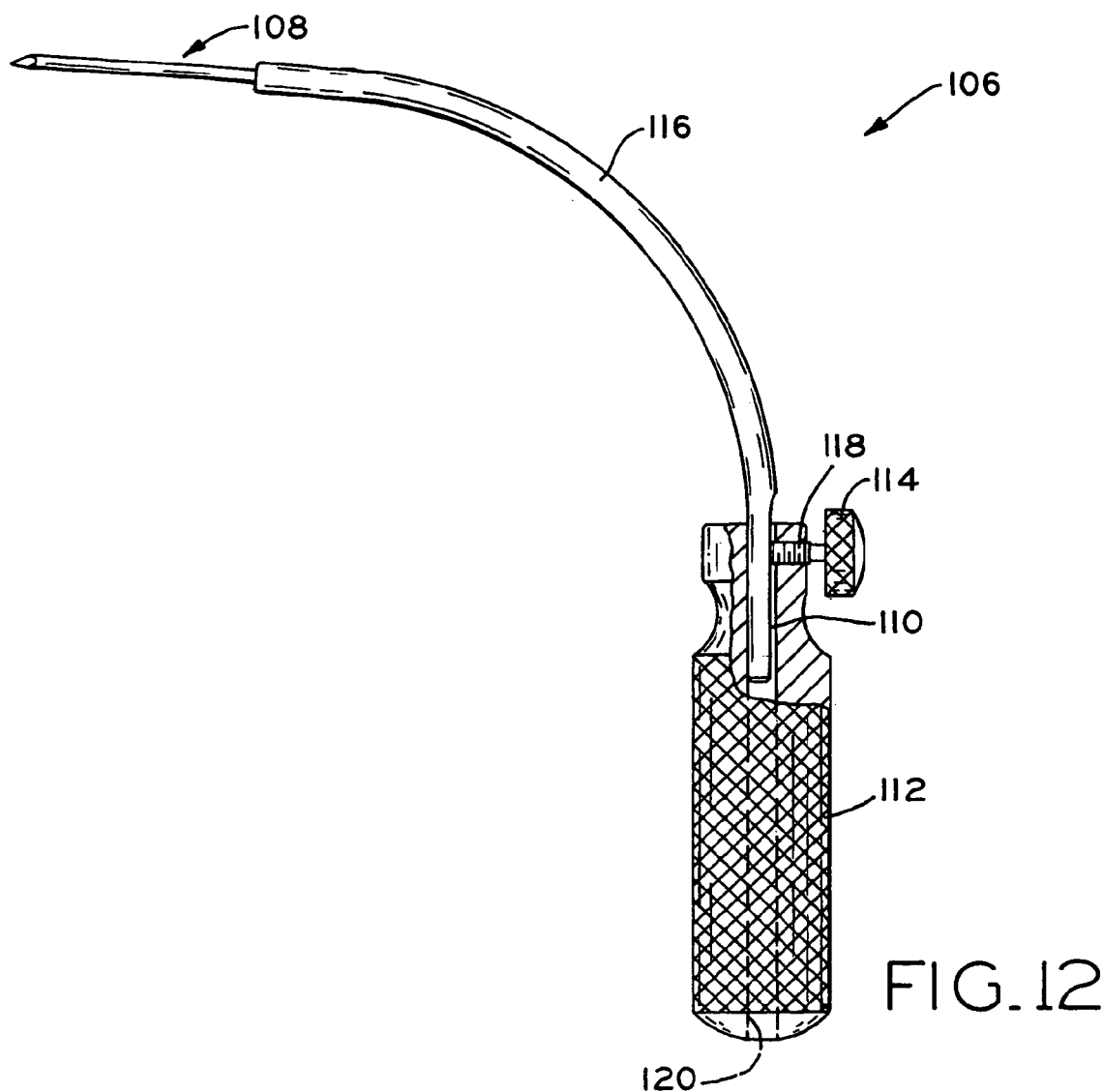
FIG. 12 is a side elevational, partial sectional view of an awl in accordance with the present invention.

As discussed supra, awl 106 (FIG. 12) is designed for insertion through anterior incision 44 to locate posterior incision 46 (FIG. 11). Awl shaft 116 includes proximal end 110 designed for insertion into handle 112. Handle 112 includes a longitudinal channel 120 into which proximal end 110 of awl shaft 116 may be inserted. Locking screw 118 is operably positioned in handle 112 and may be actuated by locking knob 114. Locking knob 114 is utilized to place locking screw 118 in locking engagement with proximal end 110 of awl 106. In one exemplary embodiment, proximal end 110 of awl 106 includes a flat portion to engage locking screw 118 and facilitate the locking engagement of awl shaft 116 to handle 112. Awl shaft 116 further includes distal end 108. Distal end 108 is generally straight and is utilized to generally align with a longitudinal axis of femur 62 (FIG. 11). As illustrated in FIG. 12, distal end 108 of awl shaft 116 includes a tapered end to facilitate insertion of awl 106 through anterior incision 44 to locate posterior incision 46. Additionally, distal end 108 of awl 106 may be of smaller diameter than the body of awl shaft 116 as illustrated in FIG. 12. In an alternative embodiment, awl 106 is formed in one piece and is disposable.

Referring now to FIG. 14, posterior retractor 122 comprises three nested parts. Guide tube 124 is nested in reamer tunnel 126 while reamer tunnel 126 is nested in rasp tunnel 130. When posterior retractor 122 is threaded into posterior incision 46, guide tube 124, reamer tunnel 126, and rasp tunnel 130 can be nested together to form a single unit. Rasp tunnel 130 includes exterior threads 132 to facilitate threading of posterior retractor 122 through posterior incision 46. Rasp tunnel 130 includes rasp aperture 134 through which reamer tunnel 126 may be inserted and, in one alternative embodiment, posterior lip 128 for positioning posterior retractor 122, as discussed above. Reamer tunnel 126 includes flange 136 which is operable to retain the position of reamer tunnel 126 within rasp tunnel 130. Reamer tunnel 126 includes reamer aperture 138 through which guide tube 124 may be inserted. Guide tube 124 includes a tapered distal end 140 to facilitate its insertion into reamer aperture 138. Guide tube 124 includes guide wire aperture 144 through which guide wire 146 (FIG. 15) may be inserted. Reamer aperture 138 is sized to allow insertion of end cutter 150 (FIG. 18), or femoral reamer 151 as discussed above. As illustrated in FIG. 18, guide tube 124 is removed from reamer tunnel 126 and end cutter 150 is inserted through reamer aperture 138. Longitudinal reamer aperture 138 is sized to accommodate guide cylinders 156 and to thereby provide guidance and stability to end cutter 150. After end cutting (and reaming, if desired) is complete, reamer tunnel 126 is removed from rasp tunnel 130. Rasp aperture 134 is sized to accommodate insertion of rasp 204 as well as cannular insertion member 168 of rasp handle 212. For surgeries which do not utilize reaming, the posterior retractor can comprise a rasp tunnel with a guide tube nested therein and not include a reamer tunnel as described above. As described above, posterior retractor 122 is not always utilized in its nested configuration. In one exemplary embodiment, guide tube 124, reamer tunnel 126, and rasp tunnel 130 are each inserted into and removed from posterior incision 46 as necessary.

Referring now to FIG. 21, rasp handle 212 includes cannular insertion member 168, impact surface 164, grip 166, elongate guide aperture 202, elongate aperture 200, and engagement channel 190. Rasp 204 includes an aperture 216 sized to receive and retain retainer 210 on distal end 208 of flexible cable 192. Retainer 210 is placed in aperture 216 and flexible cable 192 follows cable channel 217 to exit rasp 204. Proximal end 194 of flexible cable 192 is inserted through elongate aperture 200 of cannular insertion member 168 and distal rasp engagement guide 206 is piloted to guide channel 215 of rasp 204. After exiting the proximal end of elongate aperture 200, proximal end 194 of flexible cable 192 may be received in engagement channel 190. Engagement channel 190 is sized to accommodate and retain retainer 196. After retainer 196 is operably positioned in engagement channel 190, grip 166 may be actuated to tension flexible cable 192.

Referring now to FIG. 20B, retainer 196 is operably positioned in engagement channel 190. Attaching means 184, such as, e.g., rivets, belts, etc. are utilized to affix biasing elements 172 to grip 166 and internal handle surface 182. Grip 166 is outwardly biased by handle biasing elements 172 and pivots about pivot point 198. Grip 166 includes tensioning member 188 and ratchet 174. Ratchet 174 is designed for engagement with tapered end 186 of pawl 176. Pawl 176 includes pawl flange 178. Spring 180 engages internal handle surface 82 and pawl flange 178 to bias pawl 176 toward cannular insertion member 168. Actuation of grip 166 against the biasing force of biasing elements 172 rotates grip 166 about pivot point 198, causes ratchet 174 to come into operative engagement with tapered end 186 of pawl 176, and causes tensioning member 188 to contact flexible cable 192. FIG. 20A illustrates grip 166 retained by pawl 176 in the closed position. As illustrated, tensioning member 188 contacts and tensions flexible cable 192, thus locking rasp 204 to rasp handle 212. Lock disengagement knob 170 can be pulled against the biasing force of spring 180 to unlock grip 166.

Referring now to FIG. 23, provisional neck 222 can be locked to rasp 204 utilizing forceps 220. Forceps 220 include blade ends 230, 232. Blade ends 230, 232 are sized for insertion into provisional head apertures 234, 236, respectively (FIGS. 24B and 24C). As illustrated in FIG. 24A, provisional neck 222 includes locking cylinder 224 and spring 228. Spring 228 upwardly biases locking cylinder 224. Upon insertion into apertures 234, 236, blade ends 230, 232 can contact tapered portion 226 of locking cylinder 224. Actuation of blade ends 230, 232 against tapered portion 226 causes locking piston 224 to move in a direction opposite to the biasing force of spring 228. Provisional neck 222 is clamped to forceps 220 and slid in a radial direction into provisional neck engagement area 218 (FIGS. 21 and 21A) on rasp 204. After provisional neck 222 is fully slid onto rasp 204, forceps 220 may be released, thereby allowing locking piston 224 to return to its locked position under the biasing force of spring 228. Rasp 204 includes circular cut outs 217 which can be engaged by locking cylinder 224 to lock provisional neck 222 in place.

Channels 225 (FIG. 24A) on provisional neck 222 accommodate protrusions 219 (FIG. 21) on rasp 204. Provisional neck 222 is slid onto rasp 204 with protrusions 219 occupying channels 225 of provisional neck 222. Stop 223 of provisional neck 222 abuts protrusions 219 when provisional neck 222 is completely slid onto rasp 204. When stop 223 abuts protrusions 219, locking cylinder 224 may be locked (i.e., forcep blades 230, 232 released) so that locking cylinder 224 engages circular cut outs 217, locking provisional neck 222 to rasp 204.

While the method of the current invention has been described with reference to a particular hip prosthesis, this is not meant to be limiting in any way and it will be understood that the method of the current invention could be used with many prosthetics, including, e.g., a cementless prosthesis, a hybrid prosthesis having a cemented stem and a cementless acetabular cup, a cemented prosthesis having both a cemented stem and a cemented acetabular cup, or an Endo prosthesis for replacing only the femoral head. In a procedure in which a cemented femoral stem is utilized, the bone cement will generally be inserted through the anterior incision. It should also be understood by those skilled in the art that in a smaller patient the method of the current invention could be performed entirely through the anterior incision with no need to make a posterior incision as described above.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of preparing an acetabulum of a hip joint to receive an acetabular component, comprising:
   making an anterior incision through skin and subcutaneous tissues to expose the hip joint, the anterior incision having a length of no more than about 5 cm;
   through the anterior incision preparing the acetabulum to receive an acetabular component through the anterior incision;
   accessing a femoral neck and a femoral head through the anterior incision; and
   cutting along the femur to remove a cut portion from a femoral shaft, said cut portion comprising the femoral head and a portion of the femoral neck.

2. The method of claim 1, wherein said step of making an anterior incision comprises making said anterior incision substantially aligned with the femoral neck.

3. The method of claim 1, wherein said anterior incision has a length of about 3.75-5 cm.

4. The method of claim 1, wherein said step of preparing the acetabulum to receive the acetabular cup through said anterior incision comprises:
   in situ morselizing said cut portion as necessary for removal through said anterior incision;
   removing said cut portion through said anterior incision; and
   reaming the acetabulum.

5. The method of claim 4, wherein said step of accessing a femoral neck and a femoral head through the anterior incision comprises steps of:
   performing a blunt dissection of muscle underlying said anterior incision to expose a capsule of a hip joint;
   incising said capsule; and
   retracting a portion of said capsule to visually expose said femoral neck.

6. The method of claim 1, wherein said step of making an anterior incision comprises making an anterior incision aligned with a longitudinal axis of the femoral neck of the femur.

* * * * *